(12) United States Patent
Schwartz et al.

(10) Patent No.: US 7,022,881 B2
(45) Date of Patent: *Apr. 4, 2006

(54) SERTRALINE HYDROCHLORIDE POLYMORPHS

(75) Inventors: Eduard Schwartz, Rechovot (IL); Tamar Nidam, Yehud (IL); Anita Liberman, Tel-Aviv (IL); Marioara Mendelovici, Rechovot (IL); Judith Aronhime, Rehovot (IL); Claude Singer, Kfar Saba (IL); Evgeni Valdman, Petah Tikva (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 0 days.

This patent is subject to a terminal disclaimer.

(21) Appl. No.: 10/861,274

(22) Filed: Jun. 4, 2004

(65) Prior Publication Data

US 2004/0220280 A1 Nov. 4, 2004

Related U.S. Application Data

(63) Continuation of application No. 09/448,985, filed on Nov. 24, 1999, now Pat. No. 6,500,987.

(60) Provisional application No. 60/110,113, filed on Nov. 27, 1998, provisional application No. 60/125,172, filed on Mar. 19, 1999, provisional application No. 60/133,117, filed on May 7, 1999, provisional application No. 60/147,888, filed on Aug. 9, 1999.

(51) Int. Cl.
*C07C 211/00* (2006.01)

(52) U.S. Cl. ..................... 564/308; 514/647
(58) Field of Classification Search ............... 564/308; 514/647

See application file for complete search history.

(56) References Cited

U.S. PATENT DOCUMENTS 6,500,987 B1 * 12/2002 Schwartz et al. ........... 564/308
6,600,073 B1 * 7/2003 Schwartz et al. ........... 564/308

\* cited by examiner

*Primary Examiner*—Samuel Barts
(74) *Attorney, Agent, or Firm*—Kenyon & Kenyon LLP

(57) ABSTRACT

The present invention is directed to forms II, III, V, VI, VII, VIII, IX and X of sertraline hydrochloride and novel methods for their preparation. According to the present invention, sertraline hydrochloride polymorph II may be produced by slurrying sertraline hydrochloride polymorph VI in aprotic organic solvent. Sertraline hydrochloride polymorphic form III may be produced by heating sertraline hydrochloride polymorphs V and VI. Sertraline hydrochloride forms V and VI may be produced from either sertraline hydrochloride or sertraline base by crystallization. Sertraline hydrochloride Form VII may be produced by suspending sertraline chloride polymorph V in water, followed by filtration. Sertraline hydrochloride Forms VIII and IX may be produced by suspending sertraline base in water followed by acidification and filtration. Sertraline hydrochloride Form X may be produced by suspending sertraline hydrochloride in benzyl alcohol with heating, followed by filtration.

6 Claims, 16 Drawing Sheets

XRD DATA FOR FORM VI

DSC OF FORM VI ETHANOLATE

X-RAY POWDER DIFFRACTOGRAM OF SERTRALINE HCL NOVEL FORM X FOR PATENT

DSC OF FORM X

SERTRALINE HYDROCHLORIDE POLYMORPHS

This application is a continuation of U.S. patent application Ser. No. 09/448,985 now U.S. Pat. No. 6,500,987, filed Nov. 24, 1999, which claims the benefit, under 35 U.S.C. §119(e) of U.S. Provisional Applications No. 60/110,113, filed on Nov. 27, 1998; No. 60/125,172, filed Mar. 19, 1999; No. 60/133,117, filed May 7, 1999 and No. 60/147,888, filed Aug. 9, 1999. All of these applications are incorporated by reference.

FIELD OF THE INVENTION

The present invention relates to novel crystalline forms of sertraline hydrochloride, (1S-cis)-4-(3,4-dichlorophenyl)-1,2,3,4-tetrahydro-N-methyl-1-naphthalenaminehydrochloride, denominated Forms VI through X, an amorphous form and novel, reproducible methods for preparing them and for preparing previously reported polymorphs II, III and V.

BACKGROUND OF THE INVENTION

Sertraline hydrochloride, (1S-cis)-4-(3,4 dichlorophenyl)-1,2,3,4-tetrahydro-N-methyl-1-naphthalenamine hydrochloride, having the formula

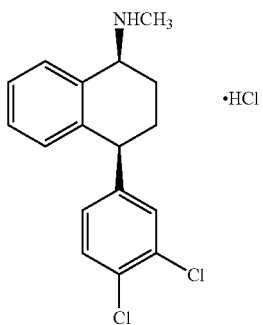

is approved, under the trademark Zoloft®, by the U.S. Food and Drug Administration, for the treatment of depression, obsessive-compulsive disorder and panic disorder.

U.S. Pat. No. 4,536,518 describes a synthesis of sertraline hydrochloride. U.S. Pat. No. 5,248,699 describes five crystalline forms of sertraline hydrochloride, designated Form I, Form II, Form III, Form IV and Form V.

U.S. Pat. No. 4,536,518 ("the '518 patent") describes the preparation of sertraline hydrochloride with a melting point of 243–245° C. by treating an ethyl acetate/ether solution of the free base with gaseous hydrogen chloride. The solid state properties of the sertraline hydrochloride so produced are not otherwise disclosed.

According to U.S. Pat. No. 5,248,699 ("the '699 patent"), the sertraline hydrochloride produced by the method of the '518 patent has a crystalline form denominated "Form II". The '699 patent discloses four other polymorphs I, III, IV, and V, and characterizes them by single crystal x-ray analysis, powder x-ray diffraction, infra-red spectroscopy, and differential scanning calorimetry. The '699 patent reports that Form II is produced by rapid crystallization of sertraline hydrochloride from an organic solvent, including isopropyl alcohol, hexane, generally describes methods for making sertraline hydrochloride Forms I–V. According to this patent, the preferential formation of Forms I, II or IV in an acidic solution consisting of isopropyl alcohol, hexane, acetone, methyl isobutyl ketone, glacial acetic acid, or preferably, ethyl acetate depends on the rapidity of crystallization. Form I is described as being made by crystallizing sertraline hydrochloride in an acidic solution using an organic solvent such as those listed above. The crystallization of Form I is carried out at a temperature from about 20° C. to about the solvent reflux temperature, preferably from about 40° to 60° C. The only method described in this patent for making Forms II and IV is by the rapid crystallization of sertraline hydrochloride from an organic solvent such as those listed above. Slow crystallization or granulation of sertraline hydrochloride will produce Form I. Form III is described as being formed by heating Forms I, II or IV to temperatures above about 180° C. Granulating either of Forms II, III or IV in isopropyl alcohol, ethyl acetate, hexane or any of the solvents listed above at a temperature from about 40° to 60° C. causes conversion to Form I. The only method described in this patent for making Form V is by sublimation of sertraline hydrochloride Form I at reduced pressure and at a temperature from about 180–190° C. onto a condenser. However, in our hands attempts to repeat this procedure to obtain Form V have been unsuccessful.

SUMMARY OF THE INVENTION

It has now been discovered that sertraline hydrochloride Form V can be formed by crystallization from various solvents rather than by sublimation. The existence of new crystal forms of sertraline hydrochloride, denominated Forms VI, VII, VIII, IX and X, and an amorphous of sertraline hydrochloride have been discovered. Form VI is a useful intermediate in the formation of previously reported sertraline hydrochloride Forms II, II and V.

The present invention also relates to sertraline hydrochloride ethanolate and processes for making sertraline hydrochloride ethanolate.

The present invention also relates to sertraline hydrochloride methanolate and processes for making sertraline hydrochloride methanolate.

The present invention also relates to sertraline hydrochloride solvate and processes for making sertraline hydrochloride solvate.

DETAILED DESCRIPTION OF THE INVENTION

Form V

Figure 1:
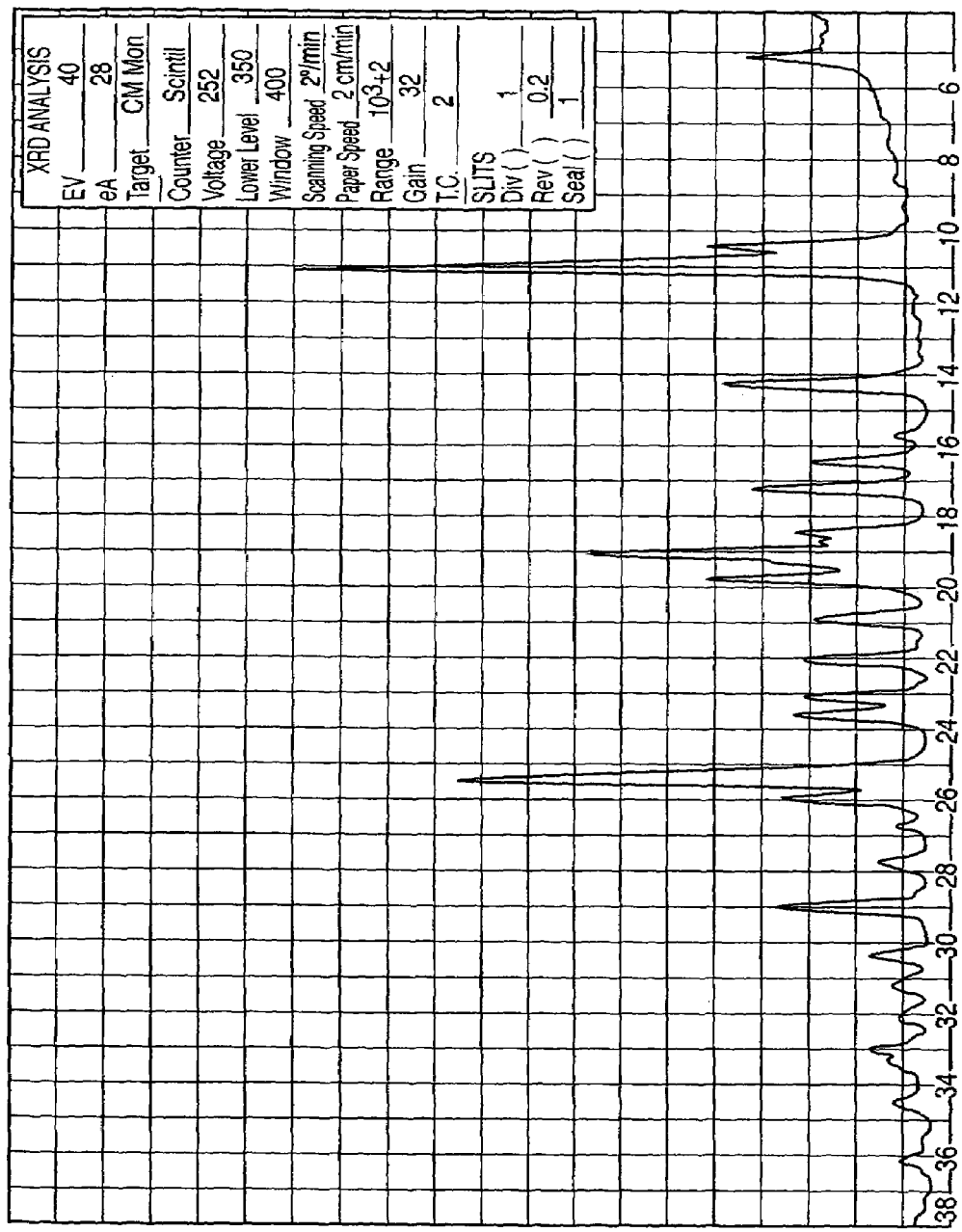
FIG. 1 is a characteristic x-ray powder diffraction spectrum of sertraline hydrochloride Form V.

The present invention provides new processes for making sertraline hydrochloride Form V from sertraline hydrochloride, sertraline base or amorphous sertraline hydrochloride. The methods provided in the present invention are more commercially practicable than the sublimation-condensation method of U.S. Pat. No. 5,248,699, which we have not been able to reproduce. It has also surprisingly been found that, by the present method, Form V is formed even at different crystallization rates.

Where the present invention provides methods for the conversion of sertraline hydrochloride to sertraline hydrochloride Form V, sertraline hydrochloride is combined with a solvent selected from the group consisting of methanol, ethanol, 1-methoxy-2-propanol and a mixture of isopropyl alcohol and water. If a mixture of isopropyl alcohol and water is used, it is preferably an about 6:1 mixture. Preferably the solvent is methanol or ethanol, and most preferably the solvent is ethanol. Sertraline hydrochloride Form V is isolated by allowing the solution to cool. One preferred method is to rapidly cool the solvent to 5° C. Another preferred method comprises seeding the solution with sertraline hydrochloride Form V crystals, followed by slow cooling to room temperature, followed by filtration and drying. Sertraline hydrochloride Form V can also be prepared by recrystallizing sertraline hydrochloride Form VI (described below) from water.

The present invention also provides methods for the conversion of sertraline hydrochloride Form II or II to sertraline hydrochloride Form V wherein the solvate sertraline hydrochloride Form VI is an intermediate. In this embodiment of the present invention, sertraline hydrochloride Form I and Form II is dissolved in either methanol or ethanol thereby forming sertraline hydrochloride Form VI. Where ethanol is the solvent, the sertraline hydrochloride Form VI is the ethanolate solvate. Where methanol is the solvent, the sertraline hydrochloride Form VI is the methanolate solvate. This intermediate sertraline hydrochloride Form VI is then dried, with or without a separate isolation step, to remove all solvent and sertraline hydrochloride Form V is isolated.

The present invention also provides methods for the conversion of sertraline hydrochloride Form II to sertraline hydrochloride Form V wherein the sertraline hydrochloride Form VIII is an intermediate. In this embodiment of the present invention, sertraline hydrochloride Form II is dissolved in water thereby forming sertraline hydrochloride Form VIII. This intermediate sertraline hydrochloride Form VIII is then dried, with or without a separate isolation step, to remove all solvent and sertraline hydrochloride Form V is isolated.

The present invention also provides methods for the conversion of sertraline base to sertraline hydrochloride Form V, wherein sertraline base is added to at least one solvent, and hydrogen chloride gas is bubbled through the solution. Preferred solvents include methanol, ethanol, water, or mixtures of ethanol, methanol, isopropyl alcohol, hexane, ethyl acetate with each other or with water. Alternatively, an appropriate amount of hydrogen chloride gas dissolved in methanol, ethanol, water, hexane, isopropyl alcohol, ethyl acetate, or a mixture thereof is combined with the sertraline base solution. Sertraline hydrochloride Form V is isolated by allowing precipitation to occur from about 0° to about 60° C. followed by filtration and drying. Preferably the solvent is hexane, isopropyl alcohol or a mixture thereof In another method, sertraline base is added to a solvent and the resulting solution is added to a hydrochloric acid solution of pH 0–4; preferably the pH of the solution is about 1.

Alternatively, sertraline base is added to a solvent selected from the group consisting of methanol, ethanol, water, hexane, isopropyl alcohol, and ethyl acetate or a mixture thereof The solution is heated and concentrated hydrochloric acid is added. Water may also be added. Sertraline hydrochloride Form V is isolated by allowing the mixture to cool to room temperature and remain at room temperature overnight, followed by filtration and drying.

Alternatively, sertraline base may be combined with a solvent selected from the group consisting of ethanol, ethanol and water, ethyl acetate, and a mixture of ethyl acetate and water. The solution is heated to about 50–60° C. and water is added. The solvent is partially removed by distillation. Sertraline hydrochloride Form V is isolated by allowing the solution to cool to room temperature, followed by filtration and drying at the precipitate.

Alternatively, sertraline base may be combined with a solvent selected from the group consisting of methanol, ethanol and a mixture thereof. A saturated solution of hydrogen chloride gas in isopropyl alcohol is added to induce formation of sertraline hydrochloride Form V. Sertraline hydrochloride Form V is isolated by allowing the solution to stand at room temperature overnight, followed by filtration and drying of the precipitate.

Sertraline base for use in the processes of the present invention may be produced by dissolving sertraline mandelate in ethyl acetate followed by neutralization of the sertraline mandelate with aqueous sodium hydroxide. The organic phase is separated from the aqueous phase and dried using magnesium sulfate. The solvent is removed under reduced pressure to produce sertraline base as an oil. Methods for making sertraline base are set forth in U.S. Pat. Nos. 4,536,518 and 5,248,699.

Where the present invention provides methods for the conversion of amorphous sertraline hydrochloride to sertraline hydrochloride Form V, amorphous sertraline hydrochloride is kept in a closed container, such as a bag, and warmed to about 40° C. to about 80° C. or is stored at room temperature for a period between a few hours and several days depending on the temperature.

The sertraline hydrochloride Form V that results from practicing the invention as exemplified herein can be characterized by its powder X-ray diffraction pattern. FIG. 1 is a representative pattern of sertraline hydrochloride Form V. The principal peaks observed are at about 5.2°±0.2, 10.4°±0.2, 11.0°±0.2, 14.3°±0.2, 16.5°±0.2, 17.3°±0.2, 18.4°±0.2, 19.1°±0.2, 19.7°±0.2, 20.9°±0.2, 22.0°±0.2, 23.2°±0.2, 23.6°±0.2, 25.5°±0.2, 26.0°±0.2 degrees 2 theta.

Three experiments were performed in order to repeat the procedure described in U.S. Pat. No. 5,248,699 for preparing Form V by sublimation. Two experiments were performed by sublimating a sample of Form I under 30 mm Hg vacuum and temperature between 170–190° C. A third experiment was performed by sublimating a sample of Form I under high vacuum (0.1 mm Hg) and temperature between 180–195° C.

Figure 2:
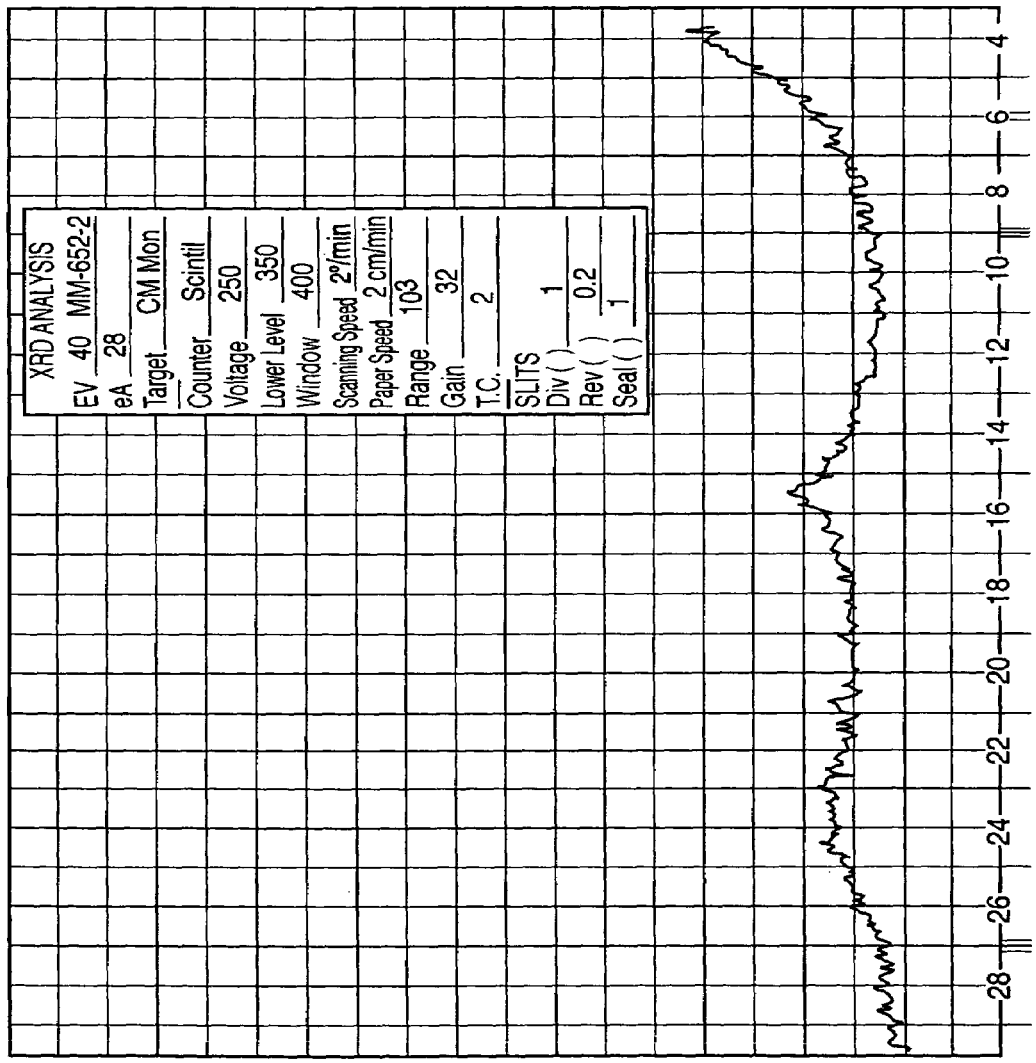
FIG. 2 is a characteristic x-ray powder diffraction spectrum of amorphous sertraline hydrochloride.

The three samples of sertraline hydrochloride prepared by sublimation were analyzed by powder x-ray diffraction. In all cases, the typical broad featureless pattern without sharp peaks typical of amorphous materials was obtained. FIG. 2 is one such pattern.

In conclusion, sertraline hydrochloride could not be obtained by following the procedure set forth in U.S. Pat. No. 5,248,699 for preparing Form V by sublimation of Form I.

Figure 4:
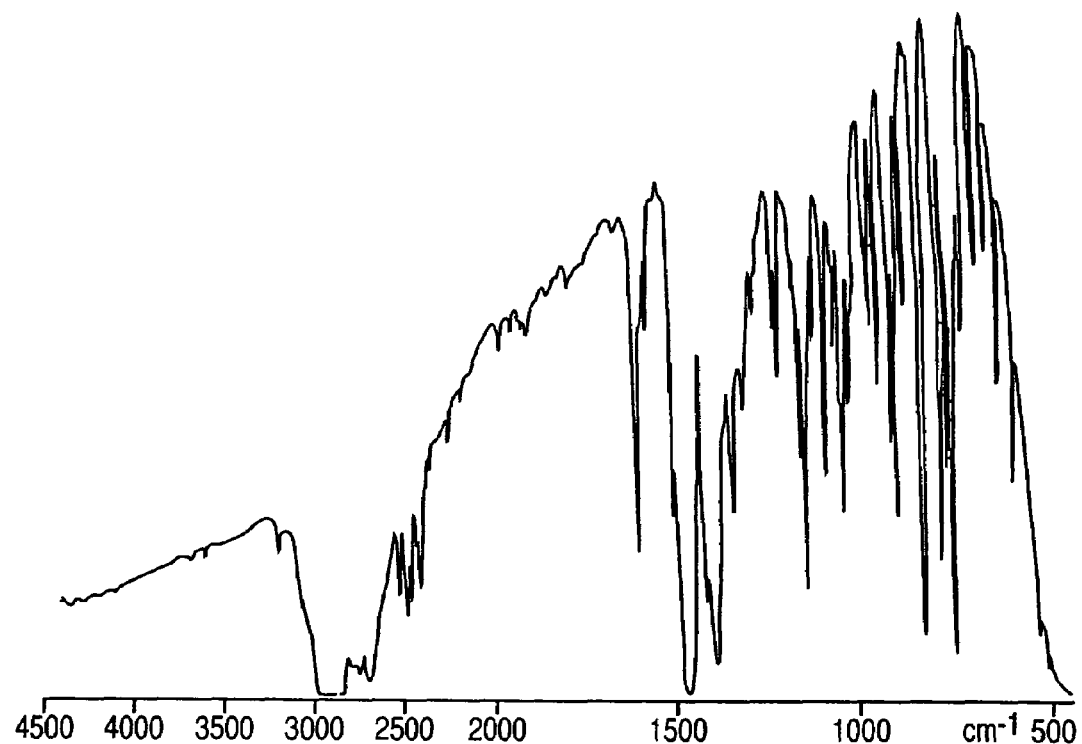
FIG. 4 is a characteristic infrared (IR) absorption spectrum of sertraline hydrochloride Form V.

The IR spectrum of sertraline hydrochloride Form V produced by the present process is characterized by the following bands: 773 cm$^{-1}$, 822 cm$^{-1}$, cm$^{-1}$, 1012 cm$^{-1}$, 1032 cm$^{-1}$, 1054 cm$^{-1}$, 1133 cm$^{-1}$, 1328 cm$^{-1}$, 1562 cm$^{-1}$, and 1590 cm$^{-1}$, as shown in FIG. 4.

Figure 3:
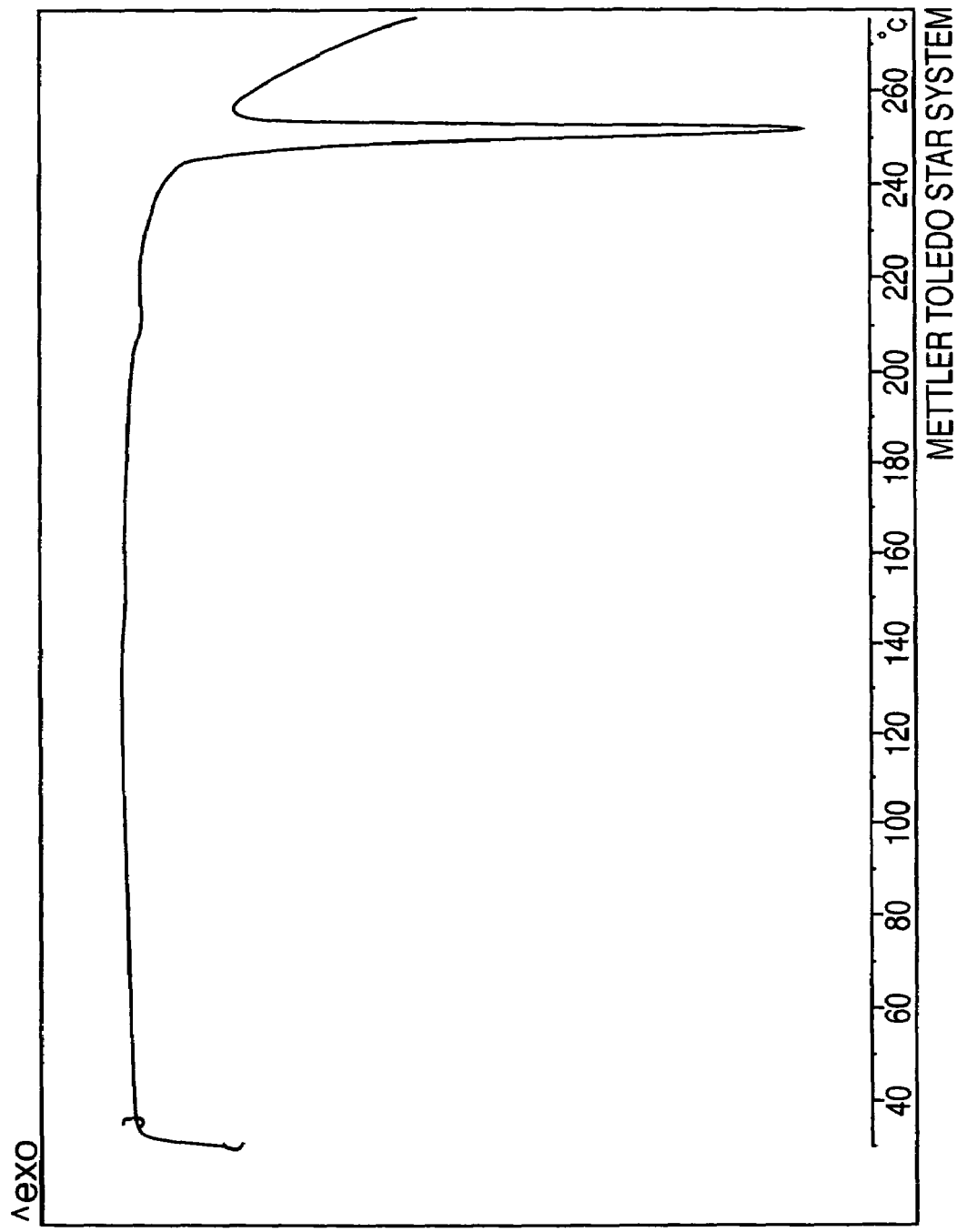
FIG. 3 is a characteristic differential scanning calorimetric (DSC) thermogram of sertraline hydrochloride Form V.

The sertraline hydrochloride Form V of the present process is further characterized by the DSC thermogram data, for example, as disclosed in FIG. 3. The DSC thermogram is characterized by a small endotherm (~3 Joule per gram) at about 210° C., believed to be a solid-solid transformation (based upon observation under a hot stage microscope) to Form III, and a melting peak. Form III at 251° C.

Form VI

Sertraline hydrochloride Form VI is a solvated crystal form of sertraline hydrochloride. In the present invention, sertraline hydrochloride Form VI may be an ethanolate; wherein ethanol is incorporated into the crystal structure of Form VI. Alternatively, sertraline hydrochloride Form VI may be a methanolate, wherein methanol is incorporated into the crystal structure of sertraline hydrochloride Form VI. All sertraline hydrochloride Form VI solvates have identical powder x-ray diffraction patterns. Therefore, when referring to sertraline hydrochloride Form VI all sertraline hydrochloride Form VI solvates such as, sertraline hydrochloride Form VI ethanolate and sertraline hydrochloride Form VI methanolate, are necessarily included.

Figure 13:
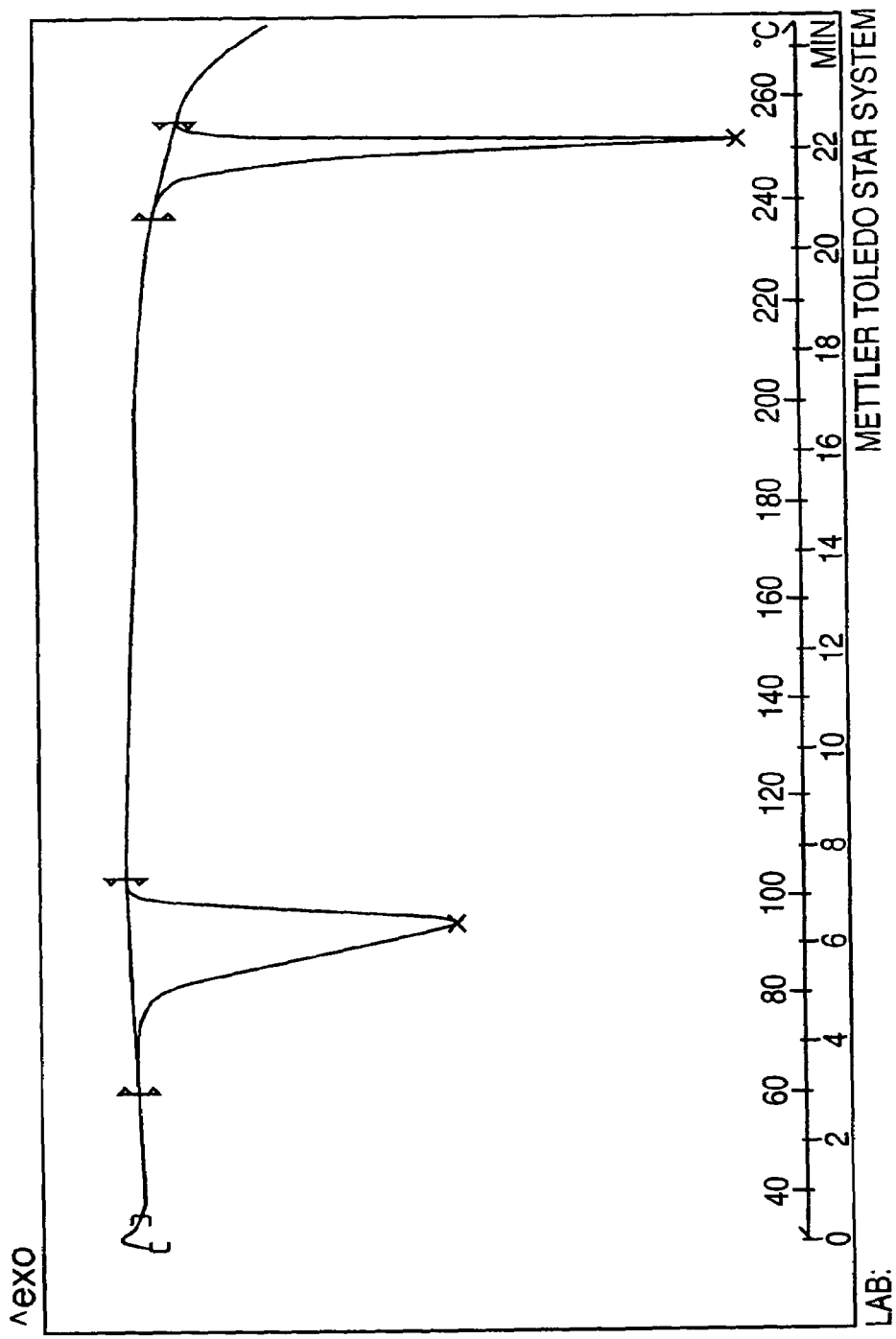
FIG. 13 is a characteristic differential scanning calorimetric (DSC) thermogram of sertraline hydrochloride Form VI.

To form the novel crystalline form sertraline hydrochloride Form VI, sertraline base is added to absolute ethanol or methanol. Hydrogen chloride gas is then bubbled through the solution. Sertraline hydrochloride Form VI is isolated by allowing precipitation to occur, followed by filtration. The DSC thermogram of Form VI crystallized from ethanol displays a desolvation peak at 95° C. (see FIG. 13) and loses 11.2% weight (by TGA); Form VI crystallized from methanol loses 8.3% weight (by TGA) upon desolvation; Form VI crystallized from ethanol is an ethanolate, and more specifically is a monoethanolate. Form VI crystallized from methanol is a methanolate, and more specifically is a monomethanolate.

The present invention also provides new processes for making sertraline hydrochloride ethanolate Form VI by reslurry of Forms I, II and V. In the conversion of sertraline hydrochloride Form I, II, V to sertraline hydrochloride ethanolate Form VI, sertraline hydrochloride Form I, II or V is dissolved or suspended in ethanol or in methanol and stirred for about 18–36 hours, 24 hours is preferred. Sertraline hydrochloride ethanolate Form VI is isolated by filtration.

Figure 5:
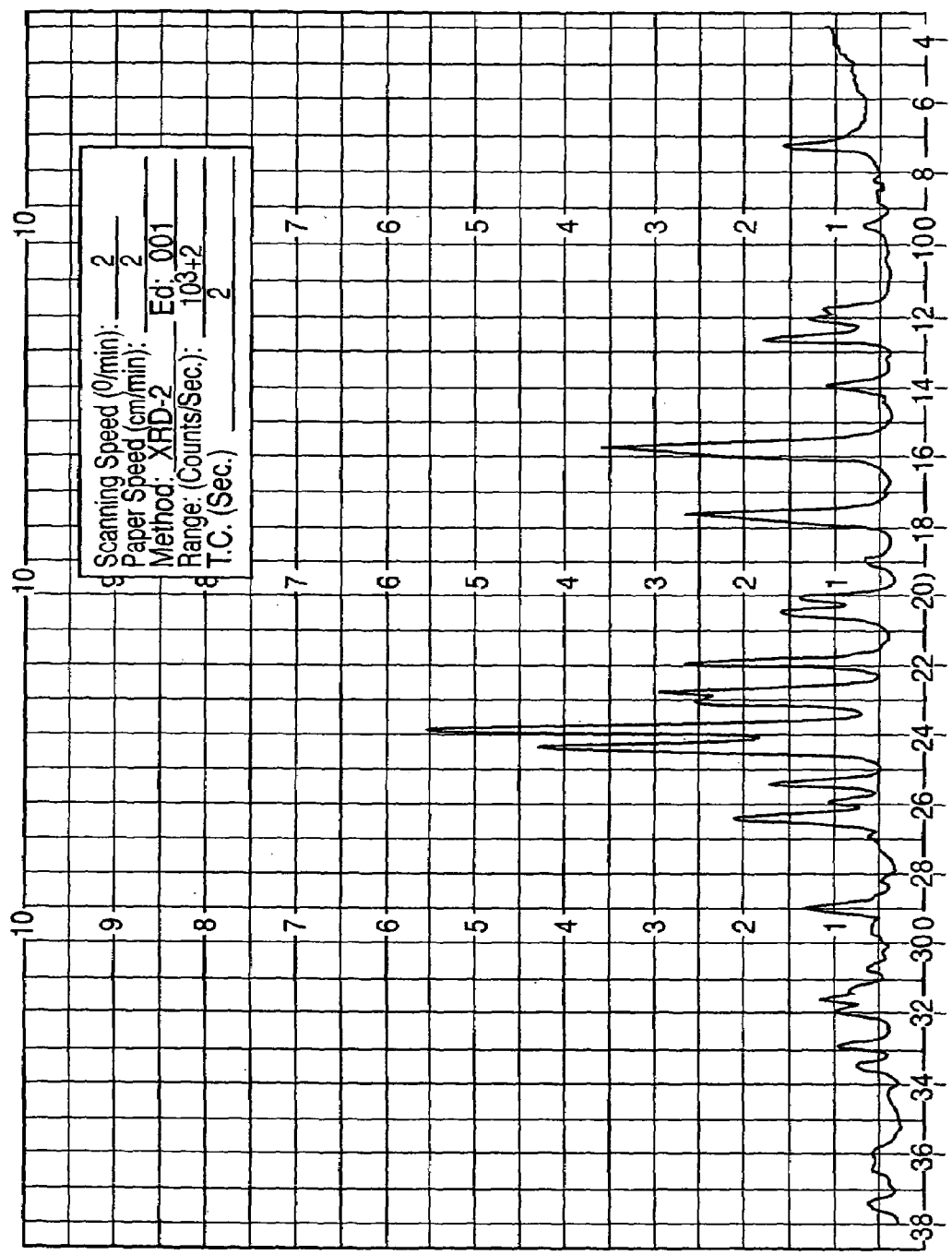
FIG. 5 is a characteristic x-ray powder diffraction spectrum of sertraline hydrochloride Form VI.

The sertraline hydrochloride Form VI so isolated exhibits the powder x-ray diffraction pattern of FIG. 5, comprising peaks at 7.3°±0.2, 12.1°±0.2, 12.7°±0.2, 14.0°±0.2, 15.6°±0.2, 17.6°±0.2, 20.1°±0.2, 20.6°±0.2, 21.9°±0.2, 22.7°±0.2, 23.0°±0.2, 23.8°±0.2, 24.3°±0.2, 25.4°±0.2, and 26.3°±0.2 degrees two-theta. Sertraline hydrochloride Form VI so obtained is a solvate. Drying of the precipitated sertraline hydrochloride Form VI at 50–60° C. overnight yields sertraline hydrochloride Form V.

Form VI

It has also been discovered that a new crystalline form of sertraline hydrochloride Form VII, may be obtained by suspending Form V in water, and filtrating the suspension after one day without further drying.

In another embodiment of the invention, sertraline hydrochloride Form VII is made from sertraline hydrochloride Form VI. Sertraline hydrochloride Form VI is dispersed in water and the mixture is heated to facilitate the dissolution of sertraline hydrochloride Form VI. The solution may be heated to about 30° C. to 90° C., preferably to about 80° C. The pH is then lowered, preferably to about pH 1 and the mixture is allowed to cool to room temperature and stirred until the reaction is complete. Preferably the reaction is stirred for two hours at room temperature. Sertraline hydrochloride Form VII is isolated by filtration and washing with water.

Figure 6:
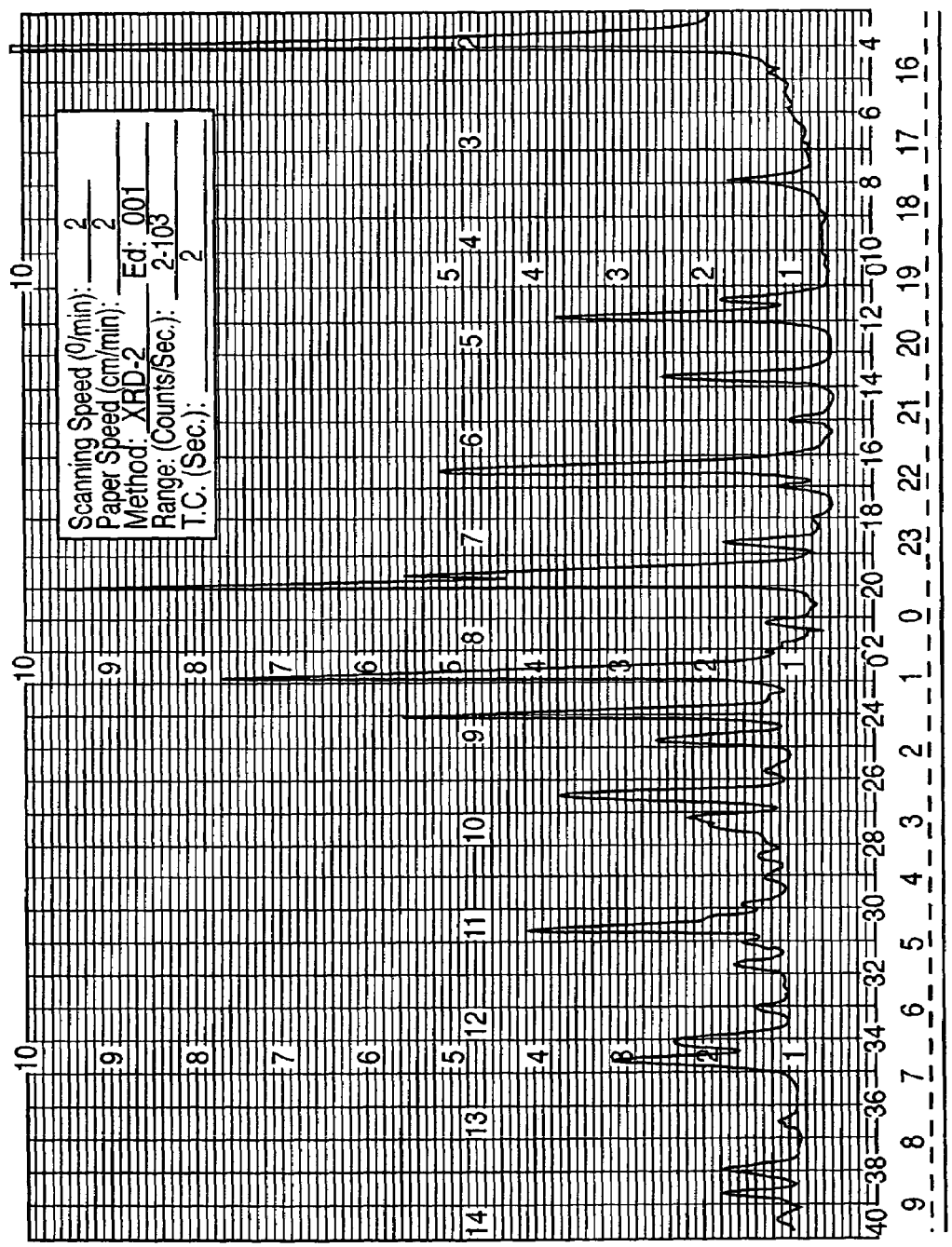
FIG. 6 is a characteristic x-ray powder diffraction spectrum of sertraline hydrochloride Form VII.

As shown in FIG. 6, sertraline hydrochloride Form VII is characterized by two unique strong x-ray powder diffraction peaks at 4.00°±0.2, and 20.0 degrees two-theta and medium intensity peaks at 8.0°±0.2, 11.6°±0.2, 12.0°±0.2, 13.8°±0.2, 16.5°±0.2, 22.8°±0.2, 24.1°±0.2, 25°±0.2, 26.60°±0.2, 30.7°±0.2, 34.7°±0.2 2 two-theta. The TGA curve shows a loss on drying of about 45%.

Forms VIII and IX

Additional new crystalline forms of sertraline hydrochloride, Forms VIII and IX, have also been discovered. Sertraline hydrochloride hydrate Form VIII may be produced by suspending sertraline base in water followed by acidification and filtration. Form IX is obtained by drying of Form VIII. Preferably the sertraline base is suspended in water, heated to approximately 80° C., adding hydrochloric acid to reduce the pH to about 1, and cooling the resulting solution to room temperature.

The present invention also provides new processes for making sertraline hydrochloride Form VIII from sertraline hydrochloride ethanolate Form VI. In one embodiment of the present invention, a slurry of sertraline hydrochloride ethanolate Form VI in water is stirred, preferably for about one hour. The slurry is then filtered and washed with water and sertraline hydrochloride hydrate Form VIII is isolated.

The present invention also provides precesses of making sertraline hydrochloride form VIII from sertraline hydrochloride Form II. In the conversion of sertraline hydrochloride Form II to sertraline hydrochloride Form VIII, sertraline hydrochloride Form II is suspended in water and stirred, preferably stirred overnight and sertraline hydrochloride hydrated Form VIII is isolated by filtration.

Figure 7:
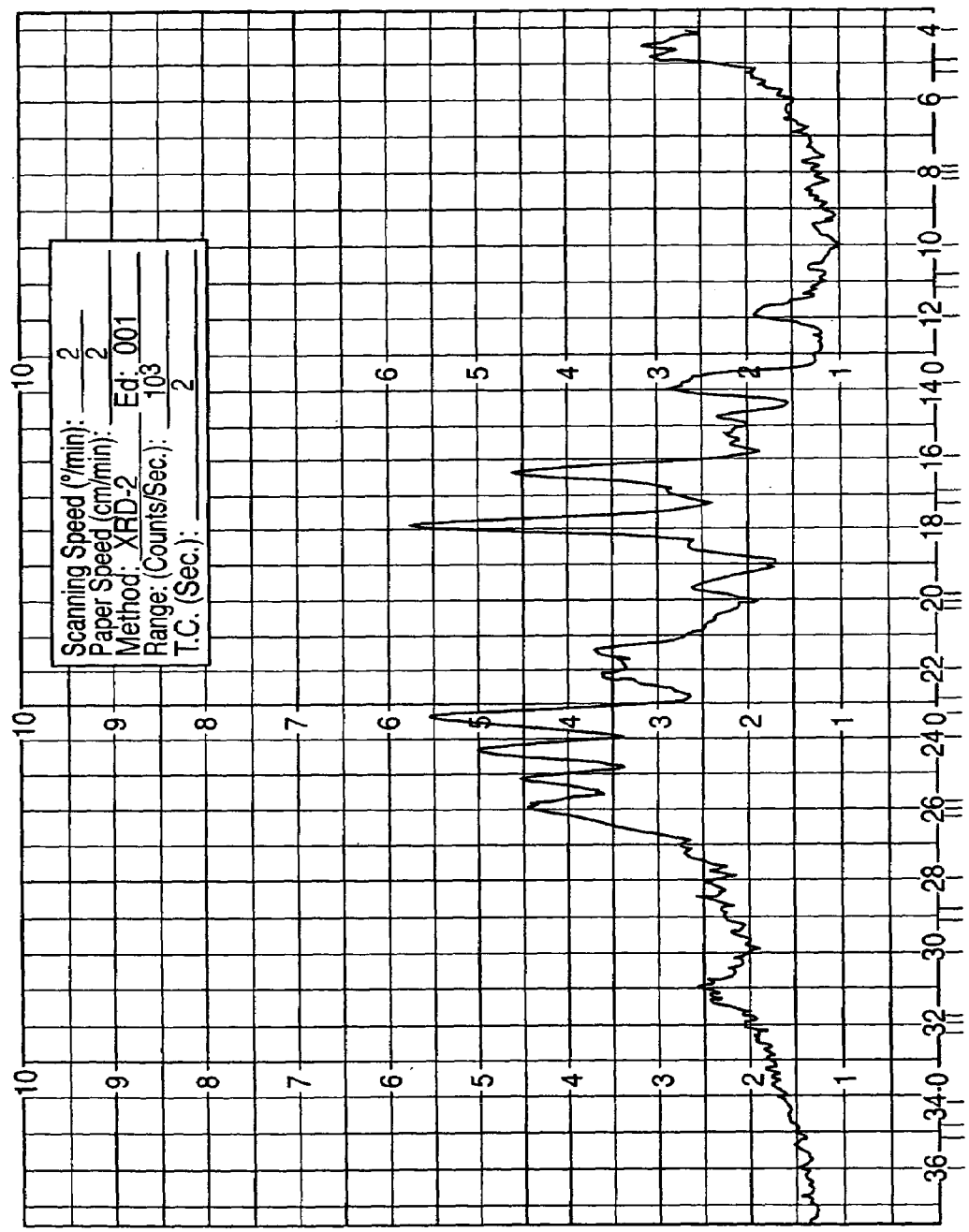
FIG. 7 is a characteristic x-ray powder diffraction spectrum of sertraline hydrochloride Form VIII.

Sertraline hydrochloride Form VIII is characterized by x-ray powder diffraction peaks at 4.7°±0.2, 11.8°±0.2, 16.3°±0.2, 17.8°±0.2, 19.6°±0.2, 23.2°±0.2, 24.2°±0.2, 25.1°±0.2, and 26.0°±0.2 two-theta, as described in FIG. 7.

Figure 9:
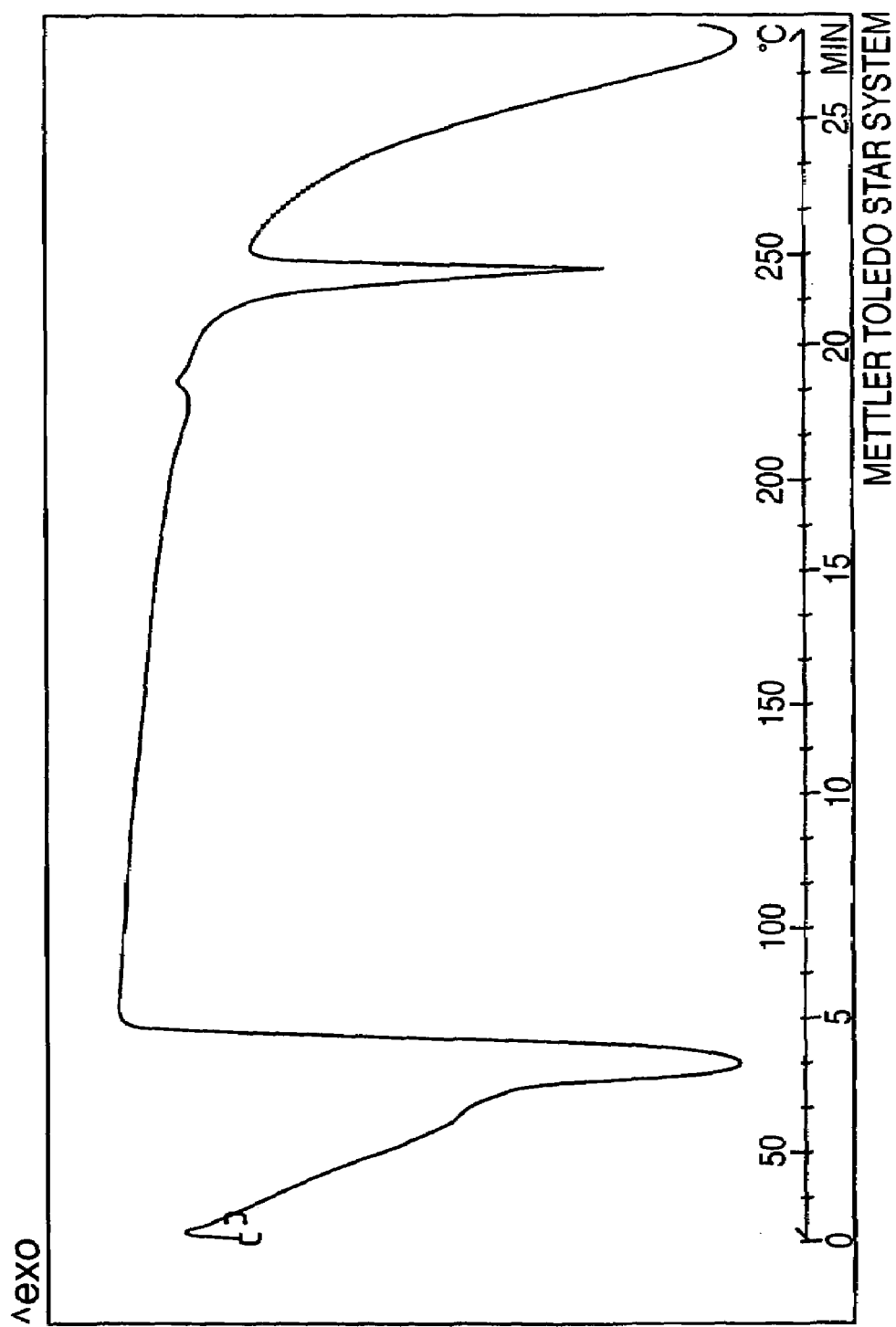
FIG. 9 is a characteristic differential scanning calorimetric (DSC) thermogram of sertraline hydrochloride Form VIII.

The DSC thermogram for Form VIII is characterized by a strong endotherm below 100° C., small endothermic and exothermic events at about 220° C. and a melting peak at 247° C. as described in FIG. 9.

The TGA curve shows a loss on drying step of about 20% below 100° C.

Figure 11:
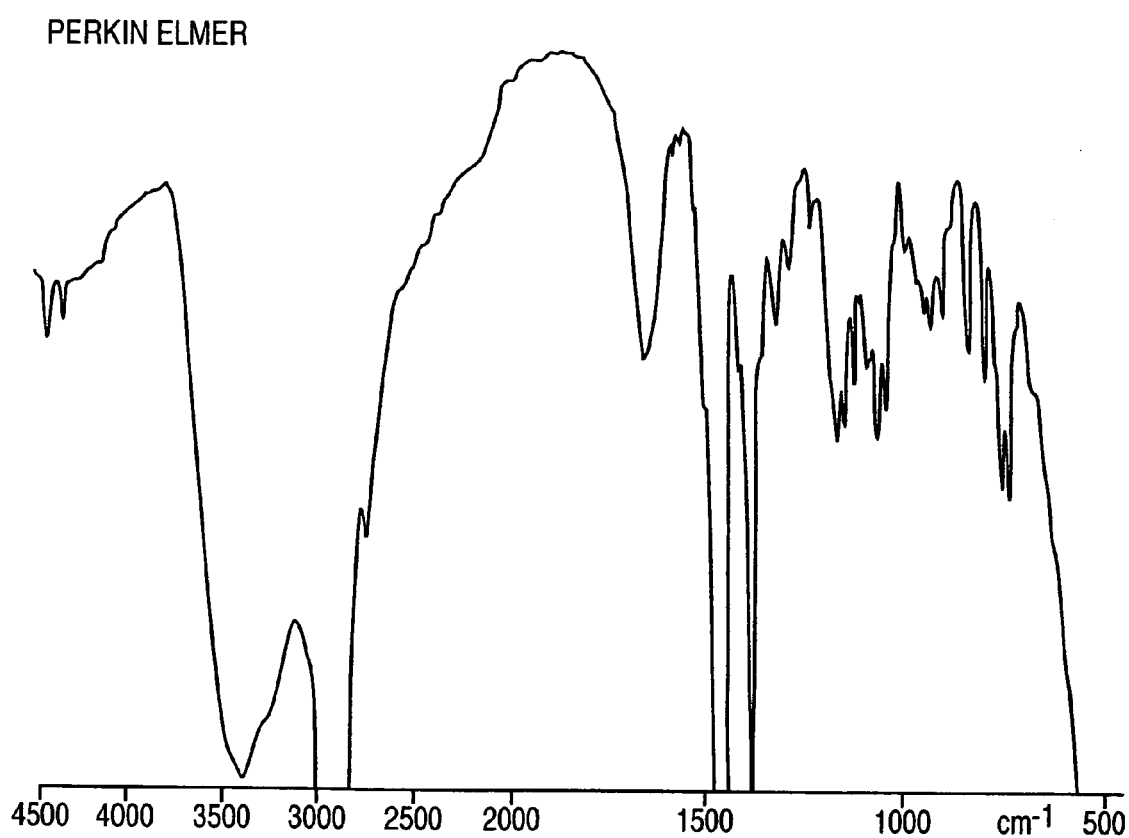
FIG. 11 is a characteristic infrared (IR) absorption spectrum of sertraline hydrochloride Form VIII.

The IR spectrum of Form VIII is characterized by the following bands: 740 cm$^{-1}$, 779 cm$^{-1}$, 822 cm$^{-1}$, 887 cm$^{-1}$, 915 cm$^{-1}$, 1031 cm$^{-1}$, 1053 cm$^{-1}$, 1110 cm$^{-1}$, 1134 cm$^{-1}$, 1153 cm$^{-1}$, 1217 cm$^{-1}$, 1307 cm$^{-1}$, and 1377 cm$^{-1}$, as described in FIG. 11.

Figure 8:
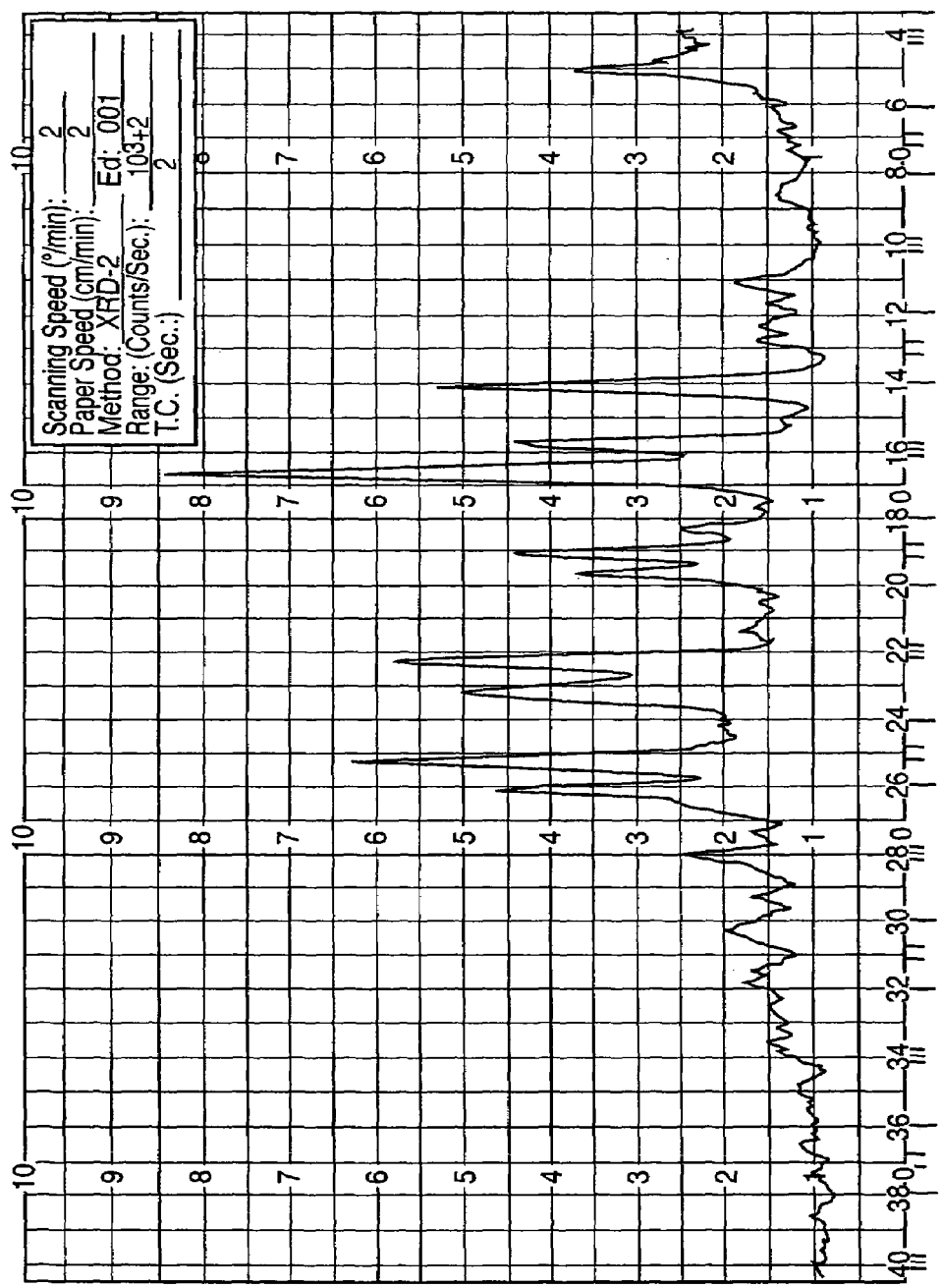
FIG. 8 is a characteristic x-ray powder diffraction spectrum of sertraline hydrochloride Form IX.

Sertraline hydrochloride Form IX is characterized by x-ray powder diffraction peaks at 5.1°±0.2, 14.2°±0.2, 15.8°±0.2, 16.8°±0.2, 19.2°±0.2, 19.7°±0.2, 22.4°±0.2, 23.2°±0.2, 25.3°±0.2 and 26.1°±0.2 two-theta, as described in FIG. 8.

Figure 12:
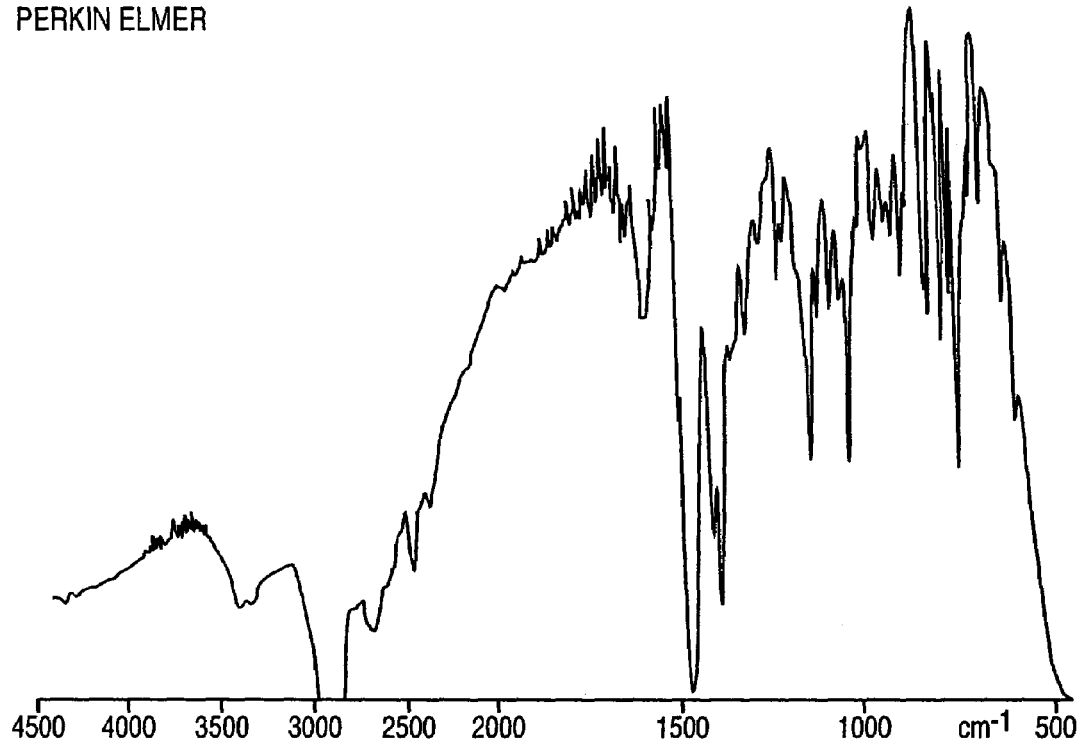
FIG. 12 is a characteristic infrared (IR) absorption spectrum of sertraline hydrochloride Form IX.

The IR spectrum of Form IX is characterized by the following bands: 701 cm$^{-1}$, 715 cm$^{-1}$, 741 cm$^{-1}$, 758 cm$^{-1}$, 780 cm$^{-1}$, 816 cm$^{-1}$, 823 cm$^{-1}$, 1030 cm$^{-1}$, 1078 cm$^{-1}$, 1110 cm$^{-1}$, 1204 cm$^{-1}$, 1217 cm$^{-1}$, 1307 cm$^{-1}$, and 1350 cm$^{-1}$, as described in FIG. 12.

Form X

It has further been discovered that another crystalline form of sertraline hydrochloride, denominated Form X, may be obtained by suspending sertraline hydrochloride in benzyl alcohol heating to facilitate dissolution. The precipitate is then filtered, washed with benzyl alcohol and dried, to yield sertraline hydrochloride Form X.

Figure 14:
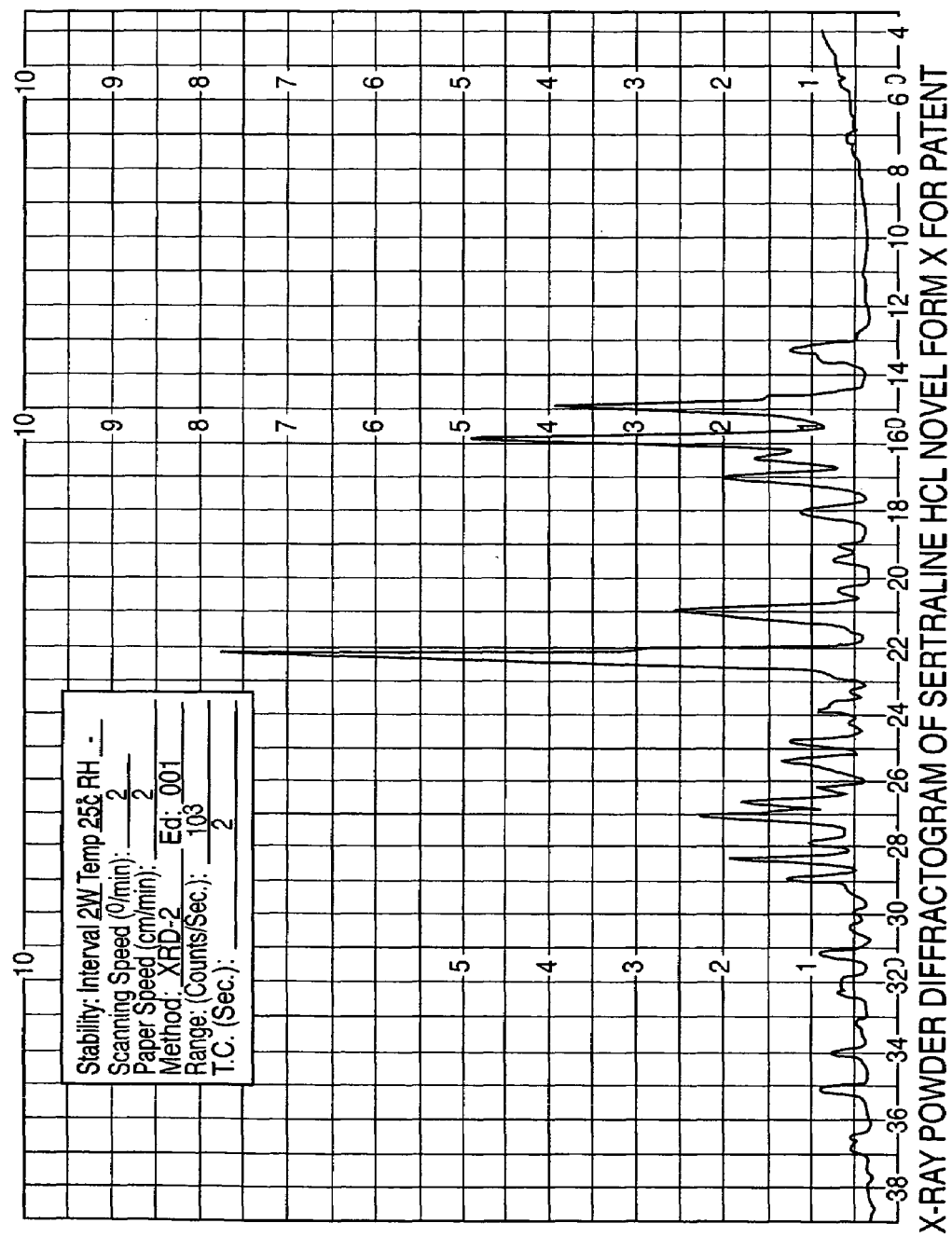
FIG. 14 is a characteristic x-ray powder diffraction spectrum of sertraline hydrochloride Form X

The Form X produced in this manner is characterized by a powder x-ray diffraction pattern having its principal peaks at 15.0°±0.2, 16.0°±0.2, 16.5°±0.2, 17.0°±0.2, 18.1°±0.2, 21.0°±0.2, 22.4°±0.2, 24.9°±0.2, 25.4°±0.2, 26.2°+0.2, 27.1°±0.2, 28.4°±0.2, and 29.0°±0.2 degrees two-theta as described in FIG. 14.

Figure 15:
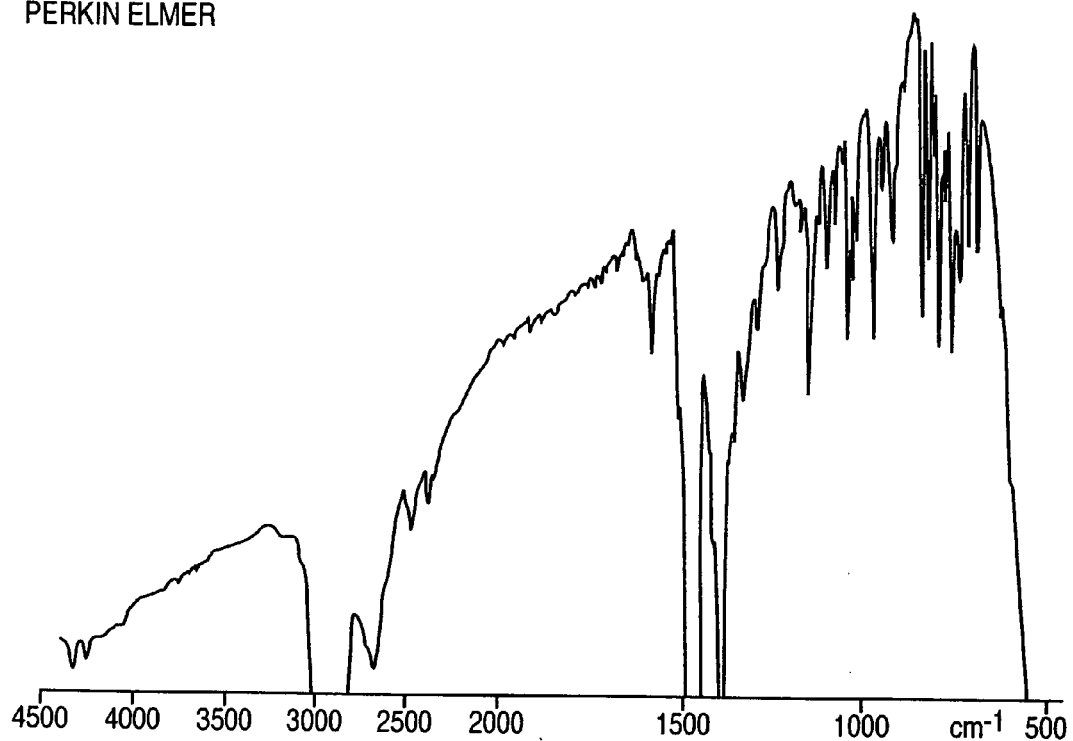
FIG. 15 is a characteristic infrared (IR) absorption spectrum of sertraline hydrochloride Form X.

The IR spectrum of Form X is characterized by the following bands: 742 cm$^{-1}$, 776 cm$^{-1}$, 806 cm$^{-1}$, 824 cm$^{-1}$, 1002 cm$^{-1}$, 1017 cm$^{-1}$, 1028 cm$^{-1}$, 1060 cm$^{-1}$, 1079 cm$^{-1}$, 1135 cm$^{-1}$, 1218 cm$^{-1}$, 1314 cm$^{-1}$, 1336 cm$^{-1}$, and 1560 cm$^{-1}$ as described in FIG. 15.

Figure 16:
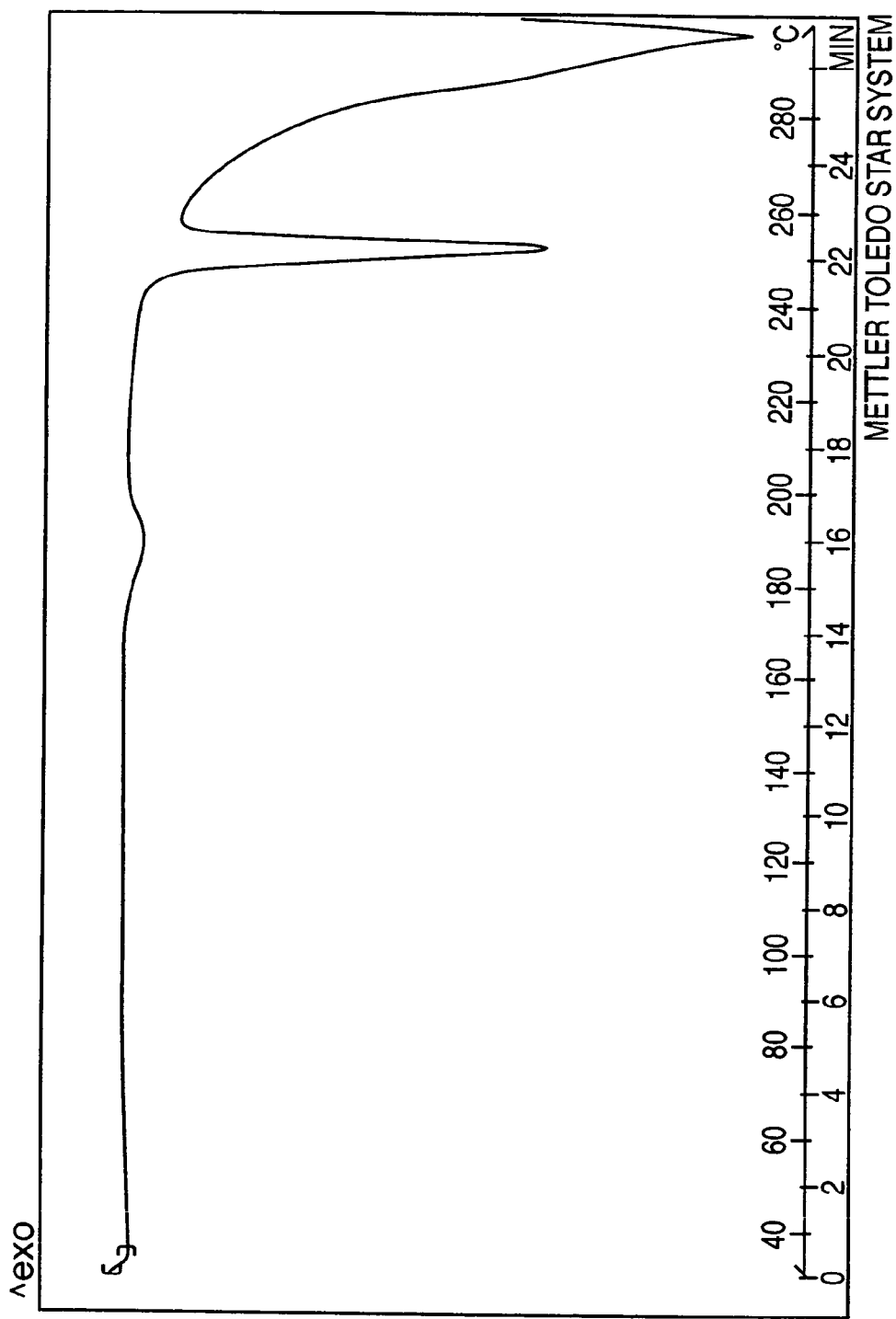
FIG. 16 is a characteristic differential scanning calorimetric (DSC) thermogram of sertraline hydrochloride Form X.

The DSC of Form X shows a small endotherm at about 190° C. followed by a melting endotherm at about 250° C., (see FIG. 16).

Form II

The present invention provides new processes for making sertraline hydrochloride Form II from sertraline hydrochloride Form VI by reslurry or granulation in organic solvents at temperatures between 25–80° C., followed by drying. The methods provided in the present invention have advantages over the rapid recrystallization method of U.S. Pat. No. 5,248,699. The method of the present invention does not require complete dissolution of sertraline hydrochloride, controlling the rate of heating or cooling of a sertraline solution, or controlling the rate of crystallization. The present method utilizes less solvent than the method of the '699 patent, since the sertraline hydrochloride starting material need not be completely dissolved.

In the conversion of sertraline hydrochloride Form VI to sertraline hydrochloride Form II, sertraline hydrochloride Form VI is combined with an aprotic organic solvent. Suitable solvents include acetone, t-butyl-methyl ether (MTBE), ethyl acetate and cyclohexane. One preferred method is to heat sertraline hydrochloride Form VI and solvent, preferably MTBE, to reflux for one hour. The slurry is cooled to room temperature and sertraline hydrochloride Form II is isolated by filtration. Another preferred method of making sertraline hydrochloride Form II comprises stirring sertraline hydrochloride Form VI and suitable solvent, preferably acetone, at room temperature for 2 hours, followed by filtration. About 1 to about 10 volumes of solvent are preferred, based on the weight of the sertraline hydrochloride starting material. See Examples 9 (3 volumes of solvent) and 10 (5 volumes of solvent) below. However, smaller amounts of solvent will also effect the transformation, albeit in some instances more slowly. The reaction is carried out for a time sufficient to convert the Form VI to Form II. We have not observed any further conversion of Form II upon treatment under these conditions for times longer than the minimum time necessary to effect the transformation.

The present invention also provides new processes for making sertraline hydrochloride Form II from sertraline hydrochloride Form V by granulation. In the conversion of sertraline hydrochloride Form V to sertraline hydrochloride Form II, sertraline hydrochloride Form V is combined with ethanol. The sertraline hydrochloride Form V ethanol mixture is stirred for at least a few hours to several days, preferably about two days to induce the formation of sertraline hydrochloride Form II.

Sertraline hydrochloride Form II may also be made by recrystallization of sertraline hydrochloride from suitable solvents such as dimethyl formamide or cyclohexanol. Sertraline hydrochloride is dissolved by warming in the solvent followed by cooling the solution at room temperature. Sertraline Form II is isolated by filtration.

The present invention also provides a new process for making sertraline hydrochloride Form II form sertraline base. Sertraline base is dissolved in a suitable such as acetone and the pH of the solution is lower by the addition of a hydrogen chloride solution, such as isopropyl alcohol and hydrogen chloride. The hydrogen chloride solution is added to induce the formation of sertraline hydrochloride Form II. Upon cooling of the mixture, for example to room temperature, sertraline hydrochloride Form II is isolated by filtration.

An experiment was performed in order to repeat the procedure described in U.S. Pat. No. 4,536,518 for preparing Form II. Sertraline base was dissolved in ethyl acetate, ether was added and the solution was acidified with hydrogen chloride gas. The material obtained after filtration and air drying was sertraline hydrochloride amorphous, not Form II as was expected.

The present invention also provides new processes for making a mixture of sertraline hydrochloride Form II and sertraline hydrochloride Form V. In this embodiment of the present invention, sertraline hydrochloride Form VI is heated to induce the transformation of sertraline hydrochloride Form VI to a mixture of both sertraline hydrochloride Form II and sertraline hydrochloride Form V. In this embodiment of the present invention, the heating of sertraline hydrochloride Form VI may be done under reduced pressure or atmospheric pressure.

Form III

The present invention provides new processes for making sertraline hydrochloride Form III from sertraline hydrochloride Form V. In the conversion of sertraline hydrochloride Form V to sertraline hydrochloride Form III, Form V is heated to a temperature between about 150° to about 180° C. for about 24 hours to induce the formation of sertraline hydrochloride Form III. The reaction may be stirred. The method of the present invention has the advantage of using no solvent.

The methods of the present invention also provides new processes for making sertraline hydrochloride Form III from sertraline hydrochloride ethanolate Form VI by heating sertraline hydrochloride Form VI at about 150° to about 180° C. for about 24 hours. The dried material is sertraline hydrochloride Form III.

Amorphous Sertraline Hydrochloride

The present invention provides new processes for making amorphous sertraline hydrochloride from sertraline hydrochloride by sublimation or by precipitating, from a non-polar solvent such as toluene, ether and t-butyl-methyl ether sertraline base.

In an embodiment of the present invention, amorphous sertraline is made by dissolving hydrochloride Form V in water and drying the solution by the spray dryer technique. Amorphous sertraline hydrochloride may also be made by sublimation of sertraline hydrochloride.

The amorphous sertraline hydrochloride produced by methods of the present invention is characterized by a powder x-ray diffraction pattern having the typical broad featureless pattern without sharp peaks typical of amorphous materials. FIG. 2 is one such pattern.

Pharmaceutical Compositions Containing Sertraline Hydrochloride Polymorphs

In accordance with the present invention, these new crystalline forms of sertraline hydrochloride and known forms of sertraline hydrochloride prepared by the new methods disclosed herein may be prepared as pharmaceutical compositions that are particularly useful for the treatment of depression, obsessive-compulsive disorder and panic disorder. Such compositions comprise one of the new crystalline forms of sertraline hydrochloride with pharmaceutically acceptable carriers and/or excipients known to one of skill in the art.

For example, these compositions may be prepared as medicaments to be administered orally, parenterally, rectally, transdermally, bucally, or nasally. Suitable forms for oral administration include tablets, compressed or coated pills, dragees, sachets, hard or gelatin capsules, sub-lingual tablets, syrups and suspensions. Suitable forms of parenteral administration include an aqueous or non-aqueous solution or emulsion, while for rectal administration suitable forms for administration include suppositories with hydrophilic or hydrophobic vehicle. For topical administration the invention provides suitable transdermal delivery systems known in the art, and for nasal delivery there are provided suitable aerosol delivery systems known in the art.

Experimental

The powder X-ray diffraction patterns were obtained by methods known in the art using a Philips X-ray powder diffractometer, Goniometer model 1050/70 at a scanning speed of 2° per minute, with a Cu radiation of $\lambda = 1.5418$ Å

The differential scanning calorimeter thermograms were obtained by methods known in the art using a DSC Mettler 821 Star°. The weight of the samples was less than 5 mg. The temperature range of scans was 30° C.–300° C. at a rate of 10° C./min. Samples were purged with nitrogen gas at a flow rate of 40 mL/min. Standard 40 µl aluminum crucibles were used having lids with three small holes.

The infrared spectra were obtained by methods known in the art using a Perkin Elmer FT-IR Paragon 1000 spectrometer. Samples were analyzed in Nujol mulls. Spectra were obtained at 4 cm$^{-1}$ resolution and 16 scans each.

EXAMPLES

The present invention will now be further explained in the following examples. However, the present invention should not be construed as limited thereby. One of ordinary skill in the art will understand how to vary the exemplified preparations to obtain the desired results.

Example 1

Preparation of Sertraline Base

Sertraline mandelate (5 g) was stirred at room temperature with 50 mL ethyl acetate. Aqueous sodium hydroxide was added dropwise until the sertraline mandelate was completely neutralized. The phases were separated and the organic phase was dried over MgSO$_4$ and filtered. The solvent was removed under reduced pressure resulting sertraline base as an oil (3.2 g).

Example 2

Preparation of Sertraline Hydrochloride Form VI and Form V

Sertraline base (25 g) was dissolved in methanol (125 mL) at room temperature. The solution was acidified with hydrogen chloride until pH 1.5 was reached. (Precipitation occurred during acidification.) The temperature rose to approximately 40° C. The slurry was allowed to cool to room temperature and stirred for about 2 hours. The solid was separated by filtration to give sertraline hydrochloride methanolate-Form VI. Drying the product overnight gave sertraline hydrochloride Form V.

Example 3

Preparation of Sertraline Hydrochloride Form VI and Form V

Sertraline base (3.2 g) was dissolved in absolute ethanol (32 mL) at room temperature and then hydrogen chloride gas was bubbled in until pH 0.5 was reached. The temperature rose to 40° C. The slurry was allowed to cool to room temperature and stirred for about 16 hours. The solid was separated by filtration, and washed with ethanol (3×2 mL). FIG. 5 sets forth the X-ray diffraction pattern of the product (sertraline hydrochloride Form VI) so obtained. Drying overnight at 50–60° C. of that product yields 2.95 g (82%) of sertraline hydrochloride Form V.

Example 4

Preparation of Sertraline Hydrochloride Form V

Sertraline base (3 g) was dissolved in absolute ethanol (15 mL) at room temperature. A saturated solution of hydrogen chloride in isopropyl alcohol was added dropwise to reach a pH of 1.3. The resulting slurry was stirred at room temperature overnight. The solid was separated by filtration and dried overnight at 50–60° C. yielding 2.75 g (81. 8%) sertraline hydrochloride Form V.

Example 5

Preparation of Sertraline Hydrochloride Form V

Sertraline base (3 g) was dissolved in absolute ethanol (15.5 mL) at room temperature and then the solution was cooled to approximately 0° C. Hydrogen chloride gas was bubbled until pH 0.5 was reached. The temperature rose to approximately 7° C. Precipitation occurred and the slurry was stirred at about 10° C. for 2 hours. The solid was isolated by filtration, washed with ethanol and dried at approximately 50° C. The dried material (2.87 g, yield 82.7%) was sertraline hydrochloride Form V.

Example 6

Preparation of Sertraline Hydrochloride Form V

Sertraline base (3 g) was stirred with 35 mL water. The slurry was heated at ~70° C. and, while maintaining this temperature, concentrated hydrochloric acid was added until pH 1 was reached. During acidification, almost complete dissolution was observed followed by precipitation. The mixture was cooled to room temperature and stirred for 2 hours. The solid was isolated by filtration, washed with water and dried overnight at 50–60° C., yielding 3.23 g (96%) sertraline hydrochloride Form V.

Example 7

Preparation of Sertraline Hydrochloride Form V

Sertraline base (3 g) was dissolved in 10 mL absolute ethanol at 40° C. The solution was heated to 50–60° C. and concentrated hydrochloric acid 32% (1.2 mL) was added until pH ~1.3 was reached. Water (12 mL) was added. The resulting clear solution was concentrated to half its volume and was allowed to cool naturally to room temperature. The solid was isolated by filtration, washed with water and dried overnight at 50–60° C., yielding 3.18 g (94.65%) sertraline hydrochloride Form V.

Example 8

Preparation of Sertraline Hydrochloride Form V

Sertraline base (3.7 g) was dissolved in 18.5 mL absolute ethanol and the solution was heated to 60° C. Hydrogen chloride gas was bubbled through the ethanol solution until pH ~0.5 was reached. The mixture was cooled to room temperature and the stirring was continued for 2 hours. The solid obtained after filtration, washing with ethanol and drying at 50° C. was sertraline hydrochloride Form V (3.16 g, yield 76%).

Example 9

Preparation of Sertraline Hydrochloride Form V

Sertraline free base was dissolved in ethanol absolute and the solution was acidified with hydrogen chloride gas to about pH 3. Precipitation occurs and the slurry was stirred at room temperature for 2 hours. The resulting solid was filtered, washed with ethanol and dried to yield sertraline hydrochloride Form V.

Example 10

Preparation of Sertraline Hydrochloride Form V

Sertraline free base (13.3 g) was dissolved in absolute ethanol (60 mL) and was added dropwise over one hour to ethanol (20 mL) containing hydrogen chloride gas (17.5 g) at 35° C. After 2 hours, the solid was filtrated, washed with ethanol and dried at about 80° C. to yield sertraline hydrochloride Form V (12.9 gr., yield 87%).

Example 11

Preparation of Sertraline Hydrochloride Form V

Anhydrous sertraline hydrochloride (2 g) was stirred with 14 mL absolute ethanol and heated to reflux to obtain a clear solution. The solution was seeded with sertraline hydrochloride Form V and cooled naturally to room temperature. Massive precipitation was observed at about 50° C. The slurry was stirred at room temperature during 2 hours. The solid was filtered, washed with ethanol (3 mL) and dried overnight at 50–60° C. yielding 1.71 g (85.5%) of sertraline hydrochloride Form V.

Example 12

Preparation of Sertraline Hydrochloride Form V

Sertraline hydrochloride ethanolate (Form VI) (40 g) in 400 mL water was heated to 80° C. and complete dissolution was obtained The pH was adjusted to approximately one with hydrochloric acid and the solution was naturally cooled to room temperature and stirred for 2 hours. The solid was filtered and dried at 50° C. for approximately 16 hours, yielding sertraline hydrochloride Form V.

Example 13

Preparation of Sertraline Hydrochloride Form V

Sertraline hydrochloride ethanolate (Form VI) (2 g) was mechanically stirred with ethanol (0.5 mL) at room temperature for 40 hours. The resulting solid was sertraline hydrochloride Form V.

Table 1 sets forth a summary of additional experiments conducted generally following procedures described above.

TABLE 1

PREPARATION OF SERTRALINE HCL - FORM V

| Exp't | Method of Crystallization | XRD | Yield (%) |
|---|---|---|---|
| | SERTRALINE BASE AS STARTING MATERIAL | | |
| A | Methanol/HCl gas | V | 78.7 |
| B | Methanol/HCl gas | V | 69 |
| C | Methanol/HCl aqueous | V | 87.8 |
| D | Ethanol/HCl gas | V | 80.9 |
| E | Water/HCl aqueous | V | 96 |
| F | Hexane/Isopropyl alcohol/HCl gas | V | 89.9 |
| G | Methanol/HCl aqueous/water | V | 89 |
| H | Isopropyl alcohol/HCl aqueous/water | V | 78 |
| I | Ethanol/HCl aqueous/evaporation of ethanol | V | 96.1 |
| J | Ethyl acetate/HCl aqueous/water/evaporation of ethyl acetate | V | 96.1 |
| K | Ethanol/isopropyl alcohol/HCl gas | V | 81.8 |
| L | Methanol/isopropyl alcohol/HCl gas | V | 82.4 |
| | SERTRALINE HCl AS STARTING MATERIAL | | |
| M | Methanol (Form I and amorphous) | V | 60 |
| N | Ethanol (Form V) | V | 85.5 |
| O | Isopropyl alcohol/water (Form V) | V | 28 |

PXRD = powder x-ray diffraction.

Example 14

Preparation of Sertraline Hydrochloride Form VII 1.003 g Sertraline hydrochloride Form V was stirred for 24 hours at room temperature in 20 mL water (HPLC grade). At the end of the stirring the mixture looked like a jelly suspension. The suspension was filtrated and the compound obtained was kept at cold conditions (4° C.) until analyzed by x-ray diffraction.

Example 15

Preparation of Sertraline Hydrochloride Form VII from Sertraline Hydrochloride Form VI A solution of sertraline hydrochloride ethanolate (Form VI) (40 g) in water (400 mL) was heated at 80° C. and complete dissolution of sertraline hydrochloride ethanolate (Form VI) was obtained. The pH was adjusted to about 1 and the solution was allowed to cool to room temperature and then stirred for 2 additional hours. The solid was isolated by filtration and washed with water to yield sertraline hydrochloride Form VII.

Example 16

Preparation of Sertraline Hydrochloride Forms VIII and IX

Figure 10:
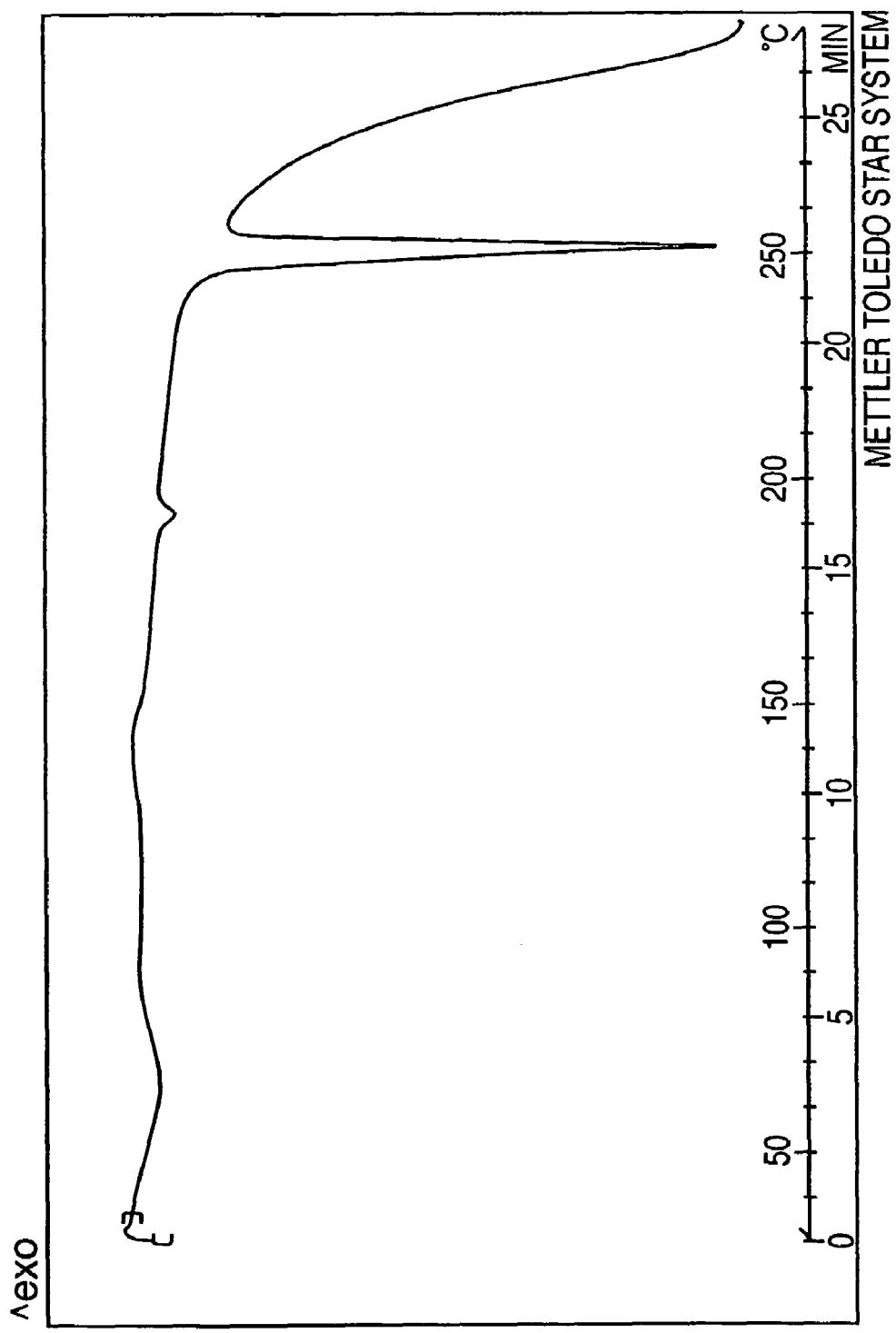
FIG. 10 is a characteristic differential scanning calorimetric (DSC) thermogram of sertraline hydrochloride Form IX.

Sertraline base (2.7 g) was suspended in 27 mL of water. This mixture was heated to 80° C. and treated with hydrochloric acid until about pH 1 was reached. A clear solution was obtained which on cooling gave a precipitate. After 2 hours stirring at room temperature the solid was isolated by filtration. This solid was characterized by powder x-ray diffraction (see FIG. 7). Drying for 24 hours at ~50° C. yielded 2.32 g (76.8%) of sertraline hydrochloride Form IX, characterized by powder x-ray diffraction, infra-red absorption, differential scanning calorimetry, and thermal gravimetric analysis as set forth above and depicted in FIGS. 8, 10, and 12.

Example 17

Preparation of Sertraline Hydrochloride Form VIII

Sertraline hydrochloride ethanolate (Form VI) (40 g) was stirred with water (80 ml.) for 1 hour at room temperature. The slurry was filtrated and washed with water to yield sertraline hydrochloride hydrate—Form VIII.

Example 18

Preparation of Sertraline Hydrochloride Form VIII from Sertraline Hydrochloride Form II Sertraline hydrochloride Form II (0.4 g) and water (8 mL) were stirred at room temperature over night. The solid was filtrated to yield sertraline hydrochloride hydrate Form VIII.

Example 19

Preparation of Sertraline Hydrochloride Form H from Form VI

A slurry of sertraline hydrochloride Form VI (50 g) and t-butyl-methyl-ether (150 ml) were heated to reflux and the reflux was continued for 1 hour. The slurry was then allowed to cool to room temperature and filtered. The solid was washed with t-butyl-methyl-ether (50 ml) and dried in a reactor under vacuum of 30 mm Hg with stirring. The dried solid so obtained is sertraline hydrochloride Form II (38.26 g: yield 86.7%).

Example 20

Preparation of Sertraline Hydrochloride Form II from Form VI

Sertraline hydrochloride Form VI (25 g) was stirred with acetone (250 ml) at room temperature for 2 hours. The solid material was filtered and washed twice with acetone (25 ml). The wet solid was dried in a vacuum agitated drier to afford sertraline hydrochloride Form II (20.09 g: yield 98.6%).

Example 21

Preparation of Polymorph II by Granulation of V

Sertraline hydrochloride Form V (2 g) and absolute ethanol (0.5 mL) were stirred in rotavapor at room temperature for 2 days. At the end of two days, the material contained sertraline hydrochloride Form II.

Example 22

Preparation of of Polymorph II by Drying of the Sertraline Hydrochloride Form VI Sertraline hydrochloride ethanolate-Form VI was dried at 105° C. under vacuum (<10 mm Hg) over 24 hours. The resulting dried material was Sertraline hydrochloride Form II mixed with sertraline hydrochloride Form V.

Example 23

Preparation of Sertraline Hydrochloride Form II

Sertraline base (3 g) was dissolved in acetone (10 mL). Isopropanol containing hydrogen chloride (20 mL) was added to the solution until the pH is ~2. The stirring was continued over night at room temperature. The resulting solid was filtrated, washed with acetone and dried to yield sertraline hydrochloride Form II (2.61 gr., yield 77.6%).

Example 24

Preparation of Sertraline Hydrochloride Form II

Sertraline hydrochloride Form V (10 gr.) was suspended in dimethylformamide (DMF) (30 mL). The heating was started and at about 70° C. a clear solution is obtained. The solution was cooled to room temperature and the solid was filtered. After drying at 80° C. for 24 hrs. Sertraline hydrochloride Form II was obtained (6.6gr.,yield 66%).

Example 25

Preparation of Sertraline Hydrochloride Form X

In a 0.1 liter three-necked bottom round flask equipped with a mechanical stirrer, a condenser and a thermometer, 30 mL benzyl alcohol is added to 10 g sertraline hydrochloride. The suspension is heated to 100° C. when a clear solution is obtained. The solution is cooled 2 hours to 25° C. and the precipitate is filtered and washed with benzyl alcohol. After drying under vacuum at 80° C. for 24 hours, 6.2 g of sertraline hydrochloride polymorph X is obtained (yield 62%). The sertraline hydrochloride Form X was characterized by powder x-ray diffraction and infrared absorption analysis as set forth above and in FIG. 14 and FIG. 15.

Example 26

Preparation of Sertraline Hydrochloride ethanolate Form VI by reslurry of Form I Sertraline hydrochloride Form I (1 g) and absolute ethanol (20 mL) were stirred at room temperature for 24 hours. Filtration of the mixture yielded sertraline hydrochloride ethanolate—Form VI.

Example 27

Preparation of Sertraline Hydrochloride Ethanolate Form VI—by Reslurry of Form II Sertraline hydrochloride Form II (1 g) and absolute ethanol (20 mL) were stirred at room temperature for 24 hours. Filtration of the mixture yielded sertraline hydrochloride ethanolate Form VI.

Example 28

Preparation of Sertraline Hydrochloride Ethanolate—Form VI—by reslurry of Form V Sertraline hydrochloride Form V (1 gr.) and ethanol absolute (20 mL.) were stirred at room temperature for 24 hrs. Filtration of the mixture yielded sertraline hydrochloride ethanolate Form VI.

Example 29

Preparation of Amorphous Sertraline Hydrochloride

Sertraline free base (10 g) was dissolved in ethyl acetate (690 mL). At room temperature, ether (690 mL) was added to the sertraline ethyl acetate solution and the solution was acidified with HCl gas to about pH 0.5. The resulting gelatinous suspension was stirred at room temperature over night. Filtration and air drying of the suspension yielded amorphous sertraline hydrochloride (9.39 gr., yield 83.8%).

Example 30

Preparation of Sertraline Hydrochloride Form III from Form V

Sertraline hydrochloride Form V was heated at 150° C. in a reactor under mechanical stirring for 24 hrs. The resulting material obtained was sertraline hydrochloride Form III.

Example 31

Preparation of Sertraline Hydrochloride from m from Form VI

Sertraline hydrochloride form VI was heated to 180° C. for 24 hours. The dried material is Sertraline hydrochloride Form III.

Example 32

Preparation of Sertraline Hydrochloride Form III from Form V

Sertraline hydrochloride Form V was heated at a temperature≧180° C. for 24 hours. The resulting material was Sertraline hydrochloride Form III.

Example 33

Preparation of Amorphous Sertraline Hydrochloride

Sertraline hydrochloride Form V (10 g) was dissolved in water (2 L) and this solution was dried by the spray dryer technique. The material obtained in this way is Sertraline hydrochloride amorphous.

Example 34

Preparation of Amorphous Sertraline Hydrochloride by Sublimation

Sertraline hydrochloride Form I was sublimated at 190–200° C., at a vacuum of 30–0.1 mm Hg, using a laboratory-type sublimator. The resulting material was amorphous sertraline hydrochloride.

A similar procedure starting from Form V also gave amorphous sertraline hydrochloride.

Example 35

Preparation of Sertraline Hydrochloride Form V from Amorphous Sertraline

Sertraline hydrochloride amorphous was heated to 80° C. for 24 hours. The resulting product was sertraline hydrochloride Form V.

Example 36

Preparation of Sertraline Hydrochloride Amorphous by Precipitation from Toluene

Sertraline base (5.8 gr.) was dissolved in toluene (200 mL). HCl gas was bubbled (about pH 1.5) through the solution. A gel is formed. Filtration and drying at 50° C. for 16 hours gives amorphous sertraline hydrochloride (6.61 gr.).

It should be understood that some modification, alteration and substitution is anticipated and expected from those skilled in the art without departing from the teachings of the invention. Accordingly, it is appropriate that the following claims be construed broadly and in a manner consistent with the scope and spirit of the invention.

What is claimed is:

1. Amorphous sertraline hydrochloride prepared by a process comprising spray drying an aqueous solution of sertraline hydrochloride.

2. A pharmaceutical composition comprising amorphous sertraline hydrochloride of claim 1 and a pharmaceutically acceptable excipient.

3. A method for the treatment of depression, comprising the step of administering to a human subject in need of such treatment the pharmaceutical composition of claim 2.

4. Amorphous sertraline hydrochloride.

5. A process for the preparation of sertraline hydrochloride in amorphous form which comprises dissolving crystalline sertraline hydrochloride in suitable solvent(s) or dissolving sertraline base in suitable solvent(s) and adding suitable solvent(s) containing hydrogen chloride and recovering sertraline hydrochloride in the amorphous form from the solution thereof by the removal of the solvent by spray drying.

6. The process of claim 5 wherein hydrogen chloride is either anhydrous and present in the gaseous form absorbed in the said suitable solvent or an aqueous solution of hydrochloric acid.

* * * * *

UNITED STATES PATENT AND TRADEMARK OFFICE
CERTIFICATE OF CORRECTION

PATENT NO.        : 7,022,881 B2
APPLICATION NO. : 10/861274
DATED               : June 4, 2004
INVENTOR(S)      : Eduard Scwartz et al.

It is certified that error appears in the above-identified patent and that said Letters Patent is hereby corrected as shown below:

Title page, item [57] Abstract: lines 11-12, change "sertraline chloride" to --sertraline hydrochloride--

Column 2, line 34, change "Forms II, II and V" to --Forms I, II and V--

Column 3, line 45, change "Form II or II" to --Form I or II--

Column 4, line 65, change "...26.0 °±0.2 degrees 2 theta." to --26.0°±0.2, and 29.1° ±0.2 degrees 2 theta.--

Column 5, line 27, change "...melting peak. Form III..." to --melting peak of Form III--

Column 6, line 7, change "Form VI" to --Form VII--

Column 6, line 30, change "...34.7°±0.2 2 two-theta..." to --34.7°±0.2 degrees two-theta--

Column 6, line 49, change "precesses" to --processes--

Column 6, line 59, change "...and 26.0°±0.2 two-theta" to --and 26.0°±0.2 degrees two-theta--

Column 7, line 7, change "...and 26.1°±0.2 two-theta" to --and 26.1°±0.2 degrees two-theta--

Column 7, line 11, change "...1030 cm$^{-1}$, 1078 cm$^{-1}$" to --1030 cm$^{-1}$, 1053 cm$^{-1}$, 1078 cm$^{-1}$--

Column 8, line 20, change "Form II form sertraline" to --Form II from sertraline--

Column 8, line 21, change "...in a suitable such as..." to --in a suitable solvent such as--

Column 9, lines 41-42, change "DSC Mettler 821 Star°" to --DSC Mettler 821 Star®--

UNITED STATES PATENT AND TRADEMARK OFFICE
CERTIFICATE OF CORRECTION

PATENT NO. : 7,022,881 B2
APPLICATION NO. : 10/861274
DATED : June 4, 2004
INVENTOR(S) : Eduard Scwartz et al.

It is certified that error appears in the above-identified patent and that said Letters Patent is hereby corrected as shown below:

Column 10, line 65, change "heated at -70°C" to --heated at ~70°C--

Column 12, line 34, change "Hexane/Isopropropyl alcohol/HCl gas" to --Hexane/Isopropyl alcohol/HCl gas--

Column 13, line 46, change "Form H" to --Form II--

Column 15, line 44, change "from m" to --Form III--

Signed and Sealed this

Thirtieth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,022,881 B2
APPLICATION NO. : 10/861274
DATED : April 4, 2006
INVENTOR(S) : Eduard Schwartz et al.

It is certified that error appears in the above-identified patent and that said Letters Patent is hereby corrected as shown below:

Title page, item [57] Abstract: lines 11-12, change "sertraline chloride" to --sertraline hydrochloride--

Column 2, line 34, change "Forms II, II and V" to --Forms I, II and V--

Column 3, line 45, change "Form II or II" to --Form I or II--

Column 4, line 65, change "...26.0 °±0.2 degrees 2 theta." to --26.0°±0.2, and 29.1° ±0.2 degrees 2 theta.--

Column 5, line 27, change "...melting peak. Form III..." to --melting peak of Form III--

Column 6, line 7, change "Form VI" to --Form VII--

Column 6, line 30, change "...34.7°±0.2 2 two-theta..." to --34.7°±0.2 degrees two-theta--

Column 6, line 49, change "precesses" to --processes--

Column 6, line 59, change "...and 26.0°±0.2 two-theta" to --and 26.0°±0.2 degrees two-theta--

Column 7, line 7, change "...and 26.1°±0.2 two-theta" to --and 26.1°±0.2 degrees two-theta--

Column 7, line 11, change "...1030 cm$^{-1}$, 1078 cm$^{-1}$" to --1030 cm$^{-1}$, 1053 cm$^{-1}$, 1078 cm$^{-1}$--

Column 8, line 20, change "Form II form sertraline" to --Form II from sertraline--

Column 8, line 21, change "...in a suitable such as..." to --in a suitable solvent such as--

Column 9, lines 41-42, change "DSC Mettler 821 Star°" to --DSC Mettler 821 Star®--

UNITED STATES PATENT AND TRADEMARK OFFICE
CERTIFICATE OF CORRECTION

PATENT NO. : 7,022,881 B2
APPLICATION NO. : 10/861274
DATED : April 4, 2006
INVENTOR(S) : Eduard Schwartz et al.

It is certified that error appears in the above-identified patent and that said Letters Patent is hereby corrected as shown below:

Column 10, line 65, change "heated at -70°C" to --heated at ~70°C--

Column 12, line 34, change "Hexane/Isopropyl alcohol/HCl gas" to --Hexane/Isopropyl alcohol/HCl gas--

Column 13, line 46, change "Form H" to --Form II--

Column 15, line 44, change "from m" to --Form III--

This certificate supersedes the Certificate of Correction issued June 30, 2009.

Signed and Sealed this

Twenty-eighth Day of July, 2009

JOHN DOLL
*Acting Director of the United States Patent and Trademark Office*